(12) United States Patent
Bonomi

(10) Patent No.: US 10,385,068 B2
(45) Date of Patent: Aug. 20, 2019

(54) SYNTHESIS PROCESS OF PRECURSORS OF DERIVATIVES OF BETA-LACTAM NUCLEI AND PRECURSORS AND DERIVATIVES THEREOF

(71) Applicant: Paolo Bonomi, Maisons-Alfort (FR)

(72) Inventor: Paolo Bonomi, Maisons-Alfort (FR)

( * ) Notice: Subject to any disclaimer, the term of this patent is extended or adjusted under 35 U.S.C. 154(b) by 0 days.

(21) Appl. No.: 15/561,908

(22) PCT Filed: Mar. 6, 2017

(86) PCT No.: PCT/IB2017/051296
§ 371 (c)(1),
(2) Date: Sep. 26, 2017

(87) PCT Pub. No.: WO2017/153892
PCT Pub. Date: Sep. 14, 2017

(65) Prior Publication Data
US 2018/0362544 A1 Dec. 20, 2018

(30) Foreign Application Priority Data
Mar. 8, 2016 (IT) .............................. UA2016A1443

(51) Int. Cl.
*C07D 499/78* (2006.01)
*C07D 499/44* (2006.01)
*C07D 501/20* (2006.01)
*C07D 499/04* (2006.01)
*C07D 501/04* (2006.01)
*C07D 501/26* (2006.01)
*C07H 19/056* (2006.01)

(52) U.S. Cl.
CPC ......... *C07D 499/78* (2013.01); *C07D 499/04* (2013.01); *C07D 499/44* (2013.01); *C07D 501/04* (2013.01); *C07D 501/20* (2013.01); *C07D 501/26* (2013.01); *C07H 19/056* (2013.01)

(58) Field of Classification Search
CPC ... C07D 499/78; C07D 499/04; C07D 499/44
See application file for complete search history.

(56) References Cited

U.S. PATENT DOCUMENTS 10,227,327 B2 * 3/2019 Rongved .............. A61K 31/444

* cited by examiner

*Primary Examiner* — Pancham Bakshi
(74) *Attorney, Agent, or Firm* — Florek & Endres PLLC

(57) ABSTRACT

A synthesis process of precursors of derivatives of beta-lactam compounds, said beta-lactam compounds being selected from 6-aminopenicillanic acid and 7-aminocephalosporanic acid, preferably 6-aminopenicillanic acid, comprising the following steps: a) protection of the amine group of the beta-lactam compound, selected from 6-aminopenicillanic acid and 7-aminocephalosporanic acid, preferably 6-aminopenicillanic acid, through the formation of a carbamate by reaction with a dicarbonate; b) esterification of the carboxyl group in position 2 of the beta-lactam compound obtained in step a) by reaction with propargyl alcohol.

16 Claims, 29 Drawing Sheets

Figure 1:
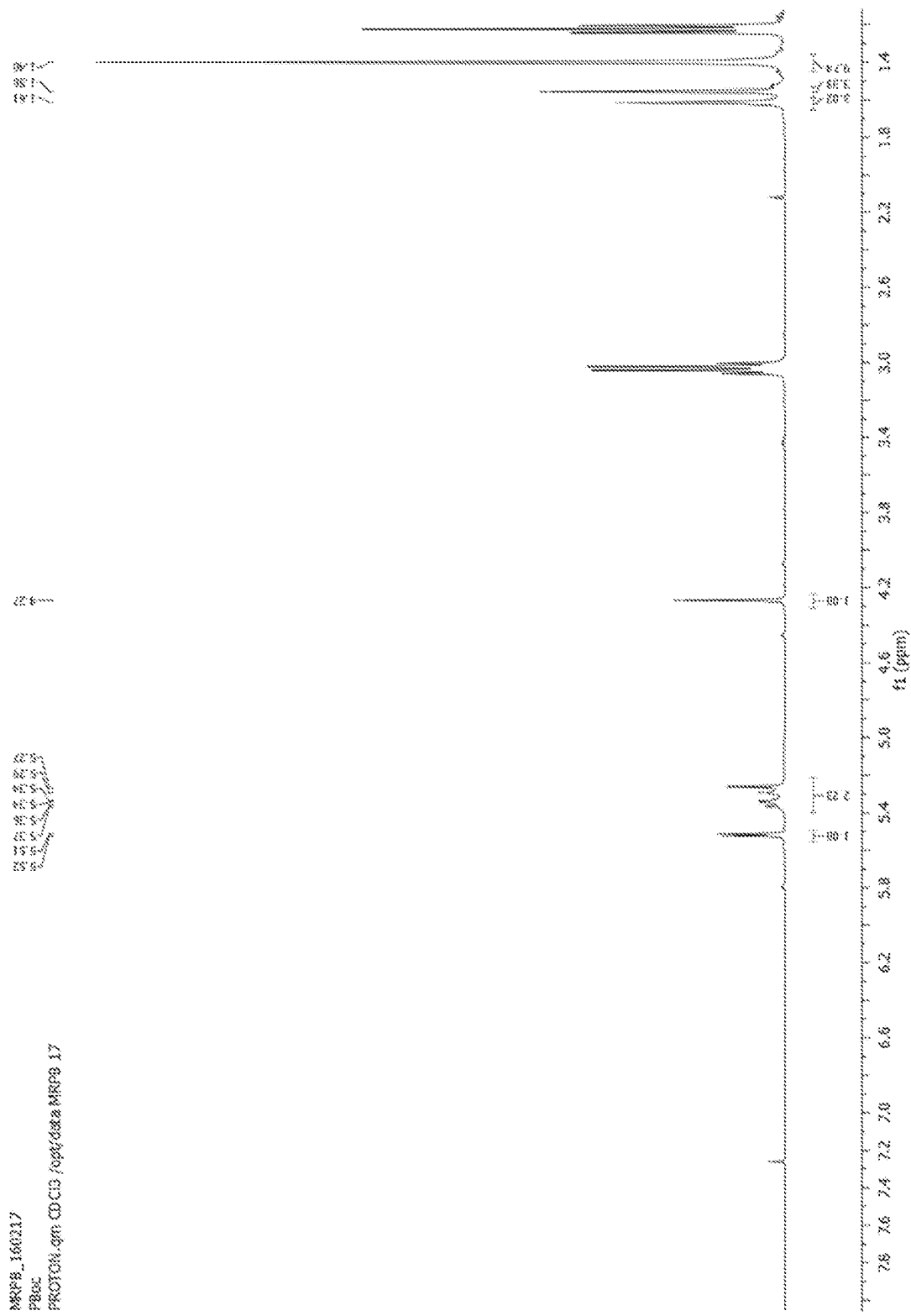
Figure 2:
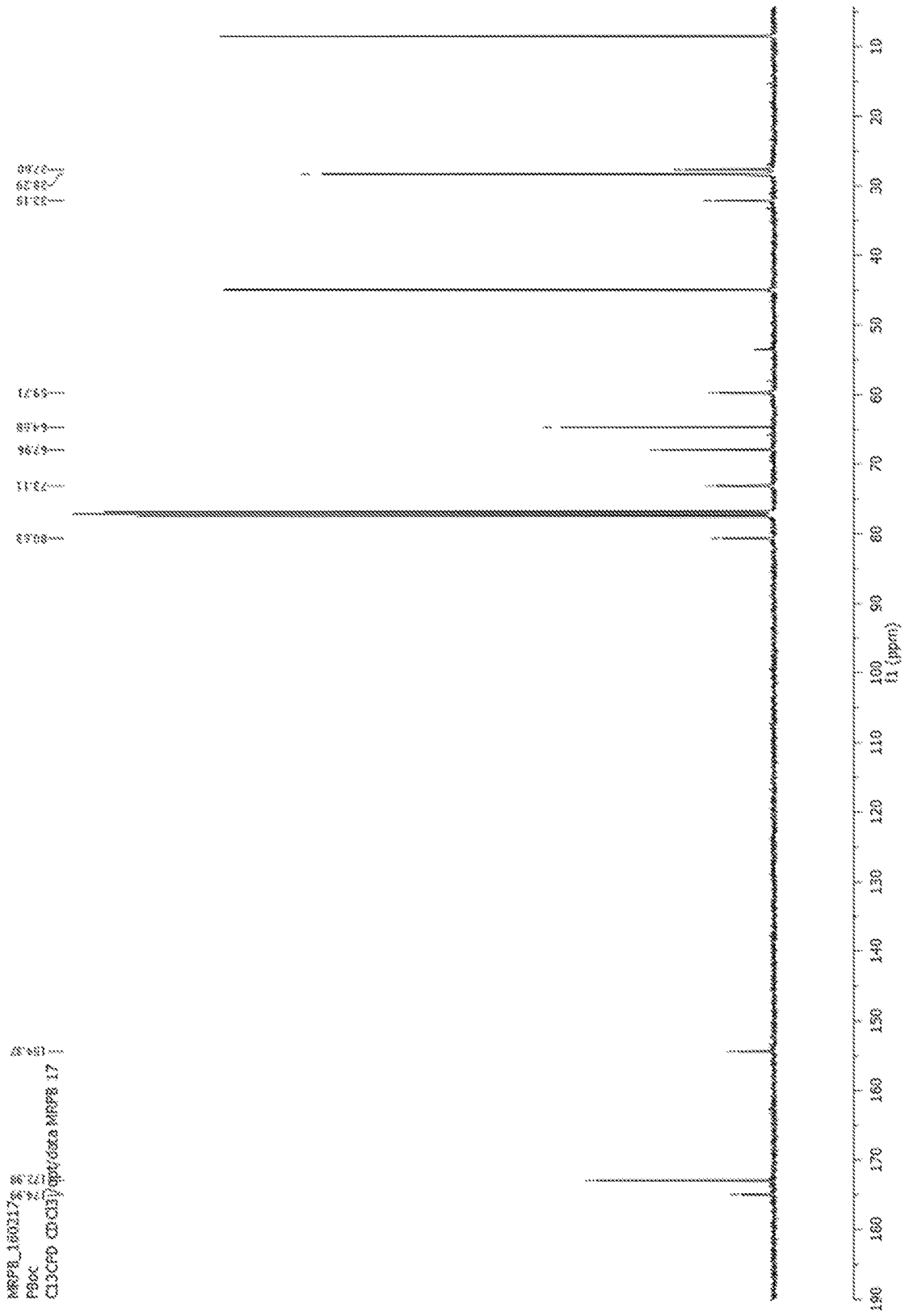
Figure 3:
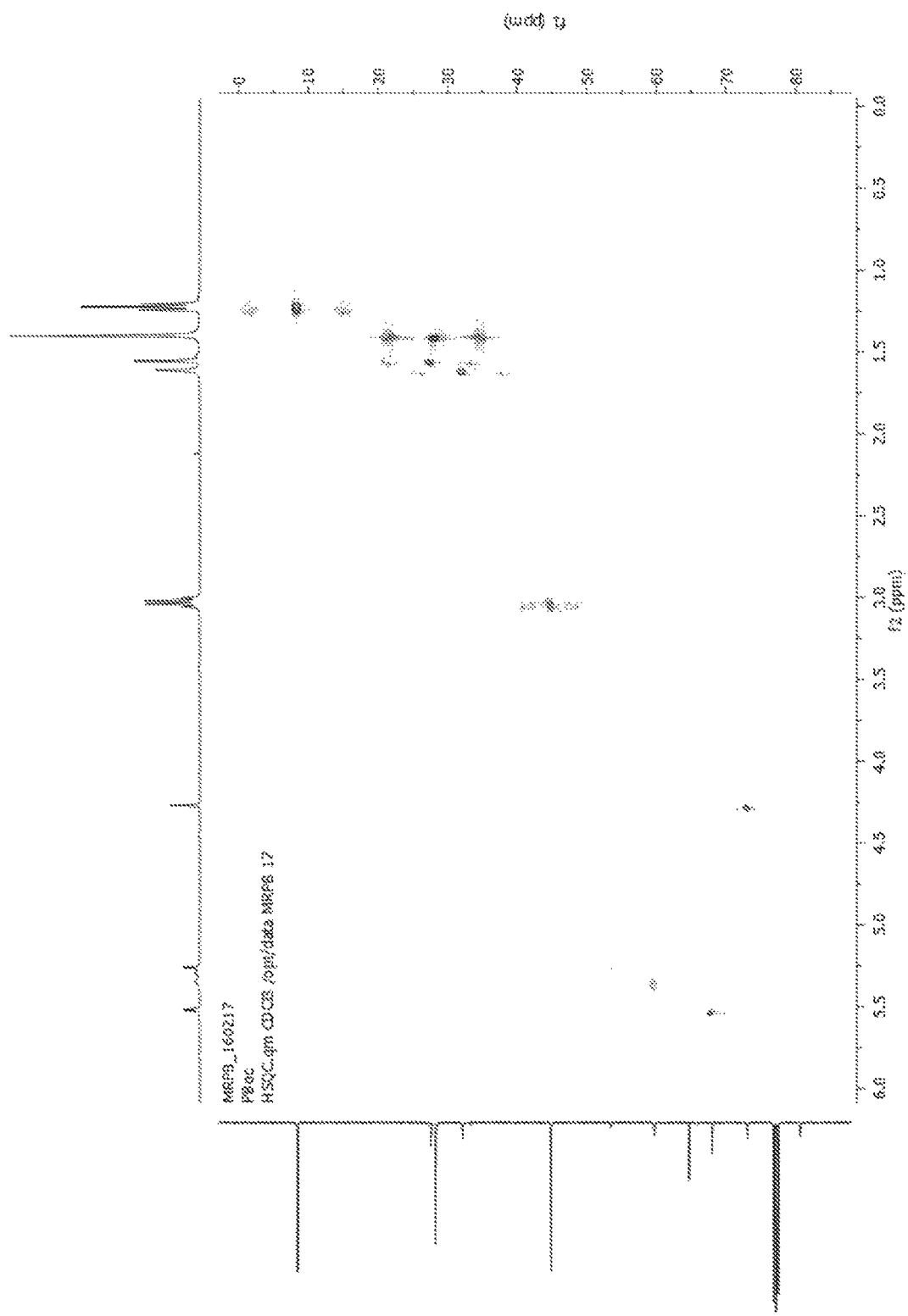
Figure 4:
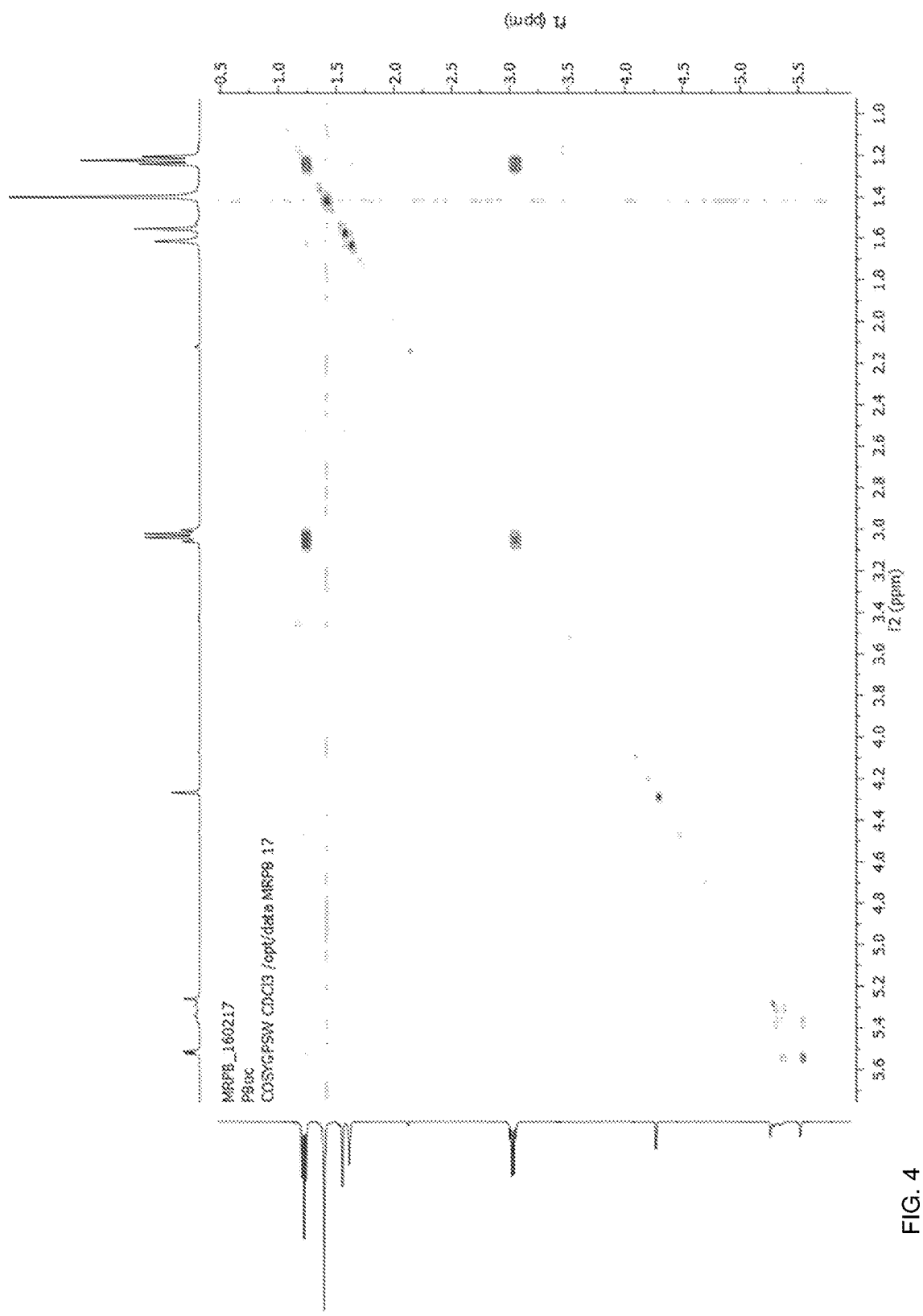
Figure 5:
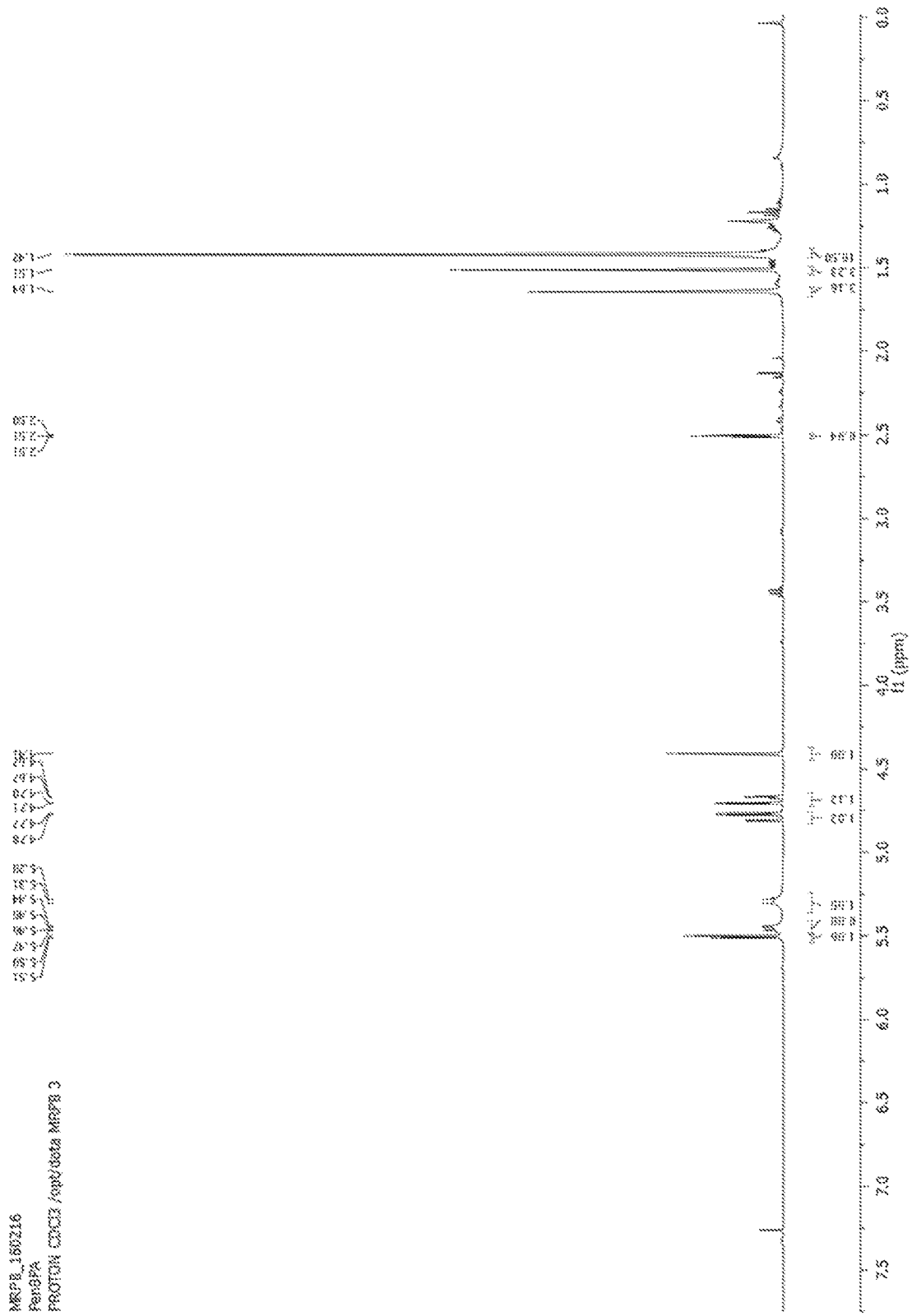
Figure 6:
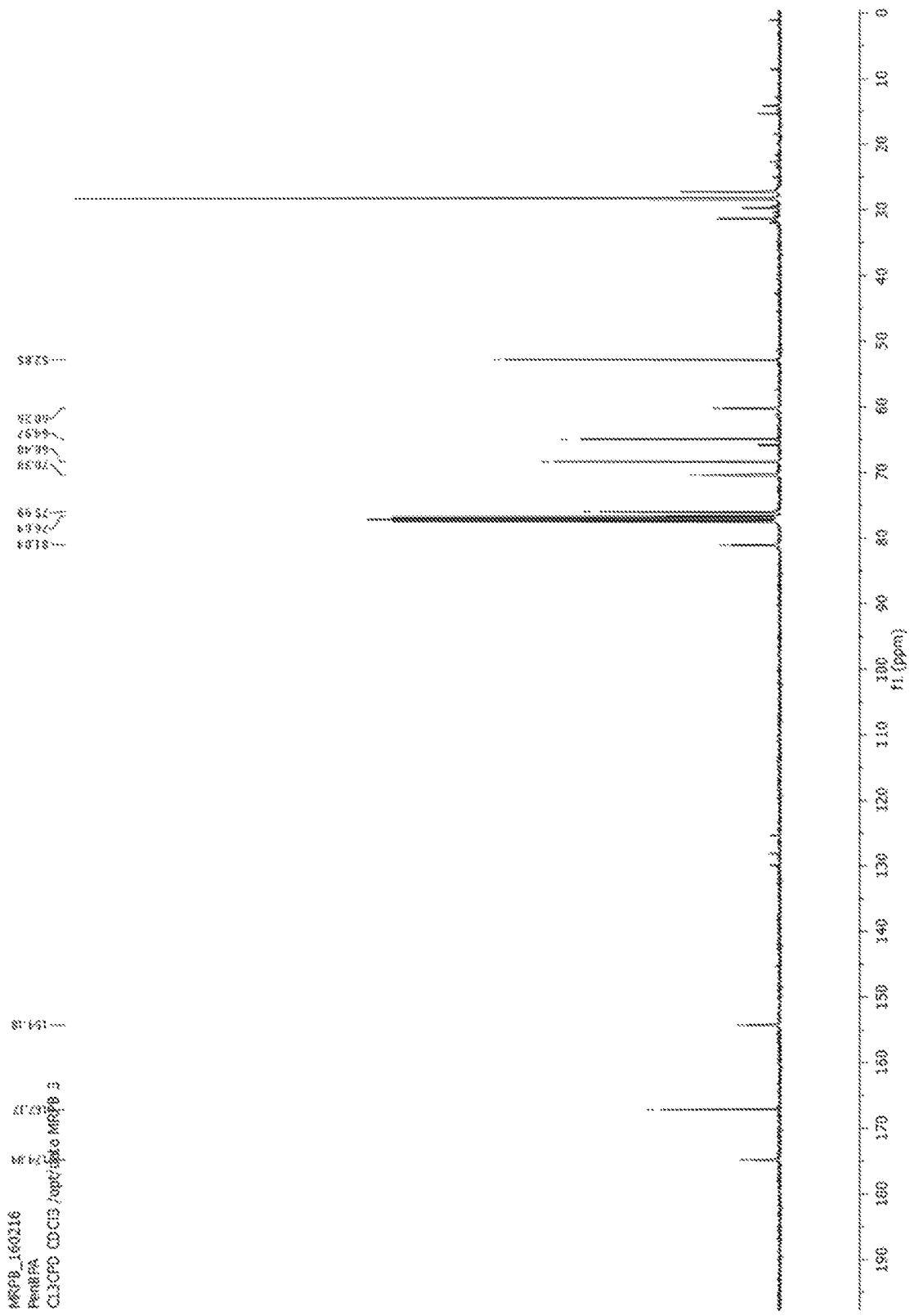
Figure 7:
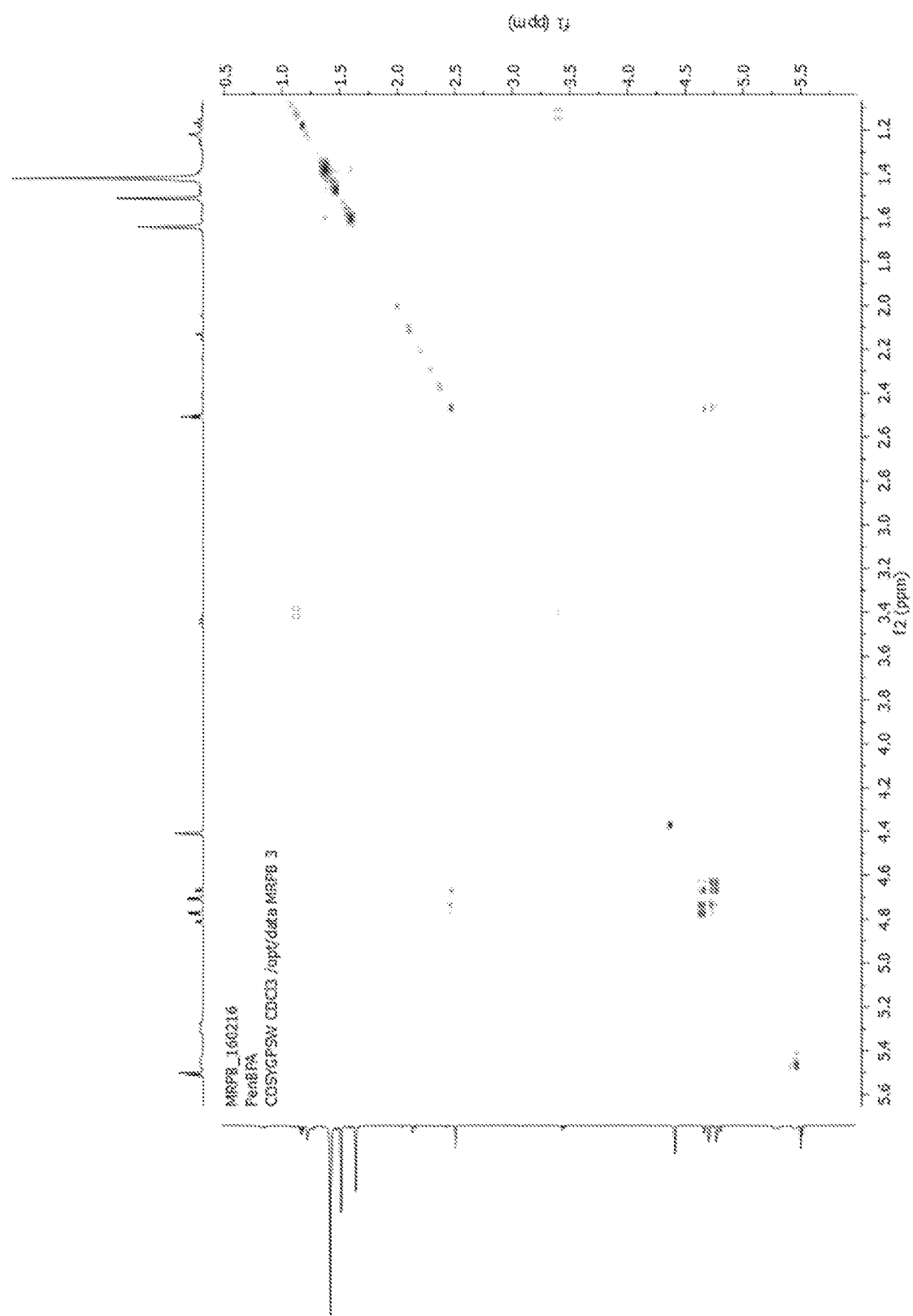
Figure 8:
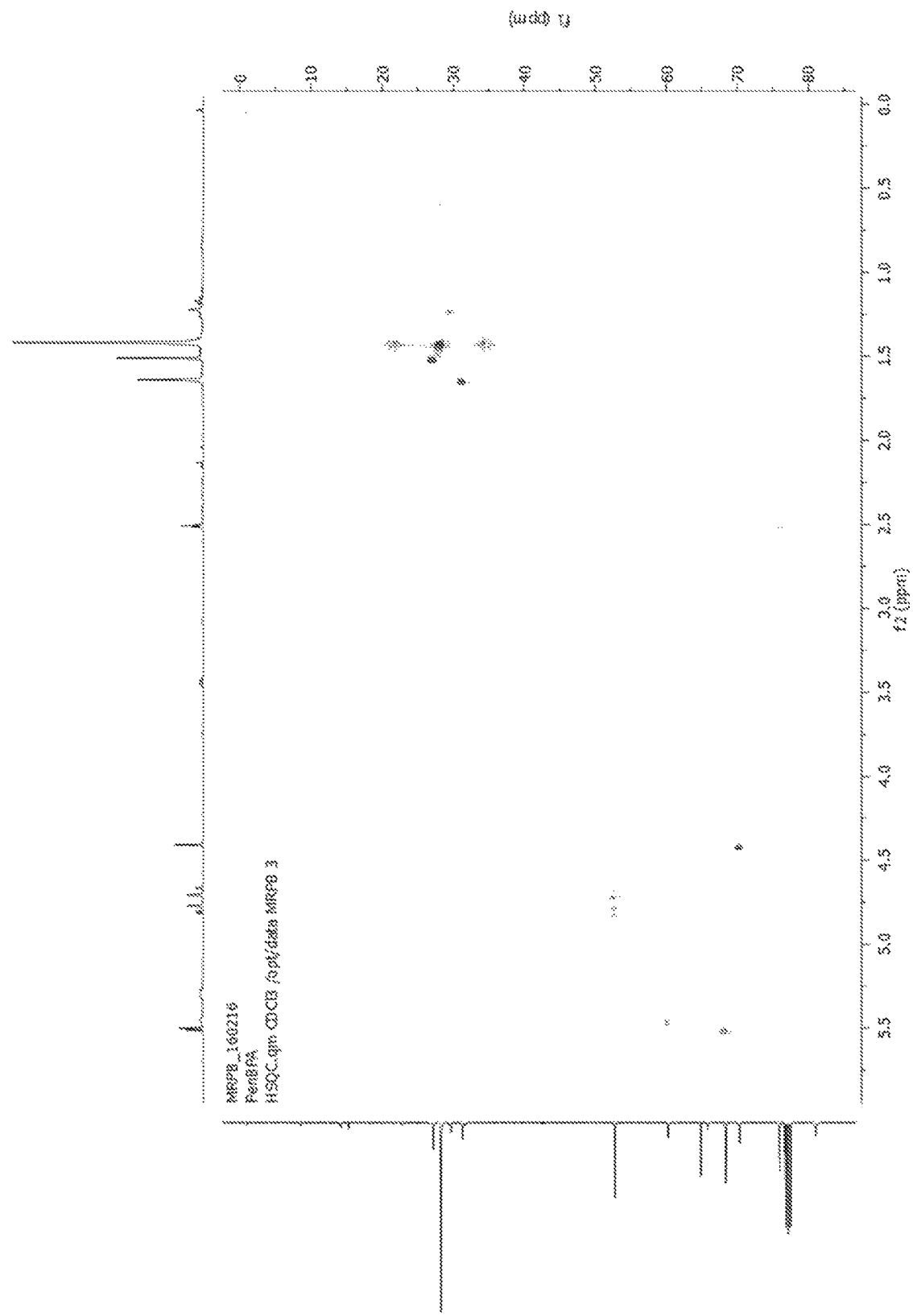
Figure 9:
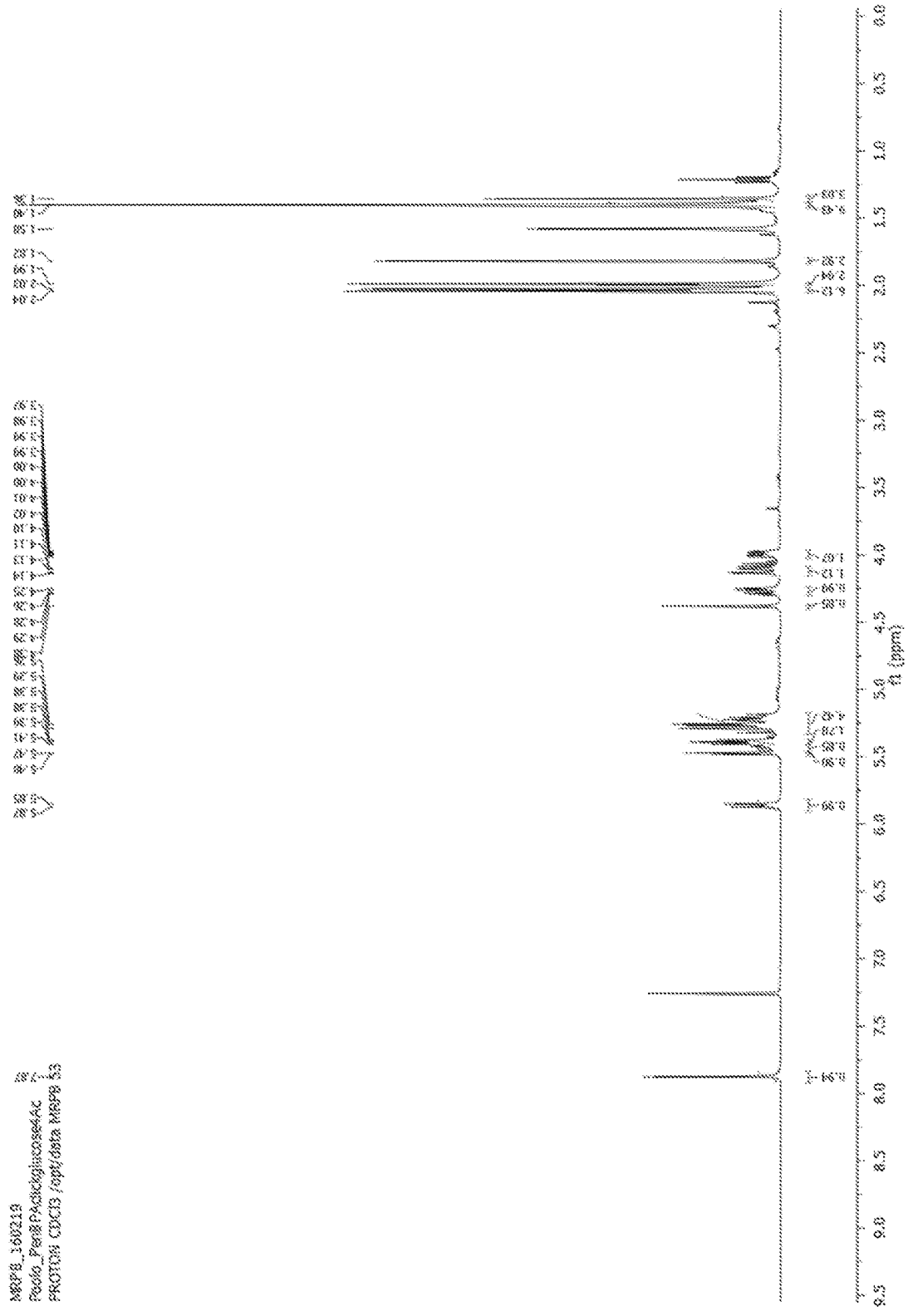
Figure 10:
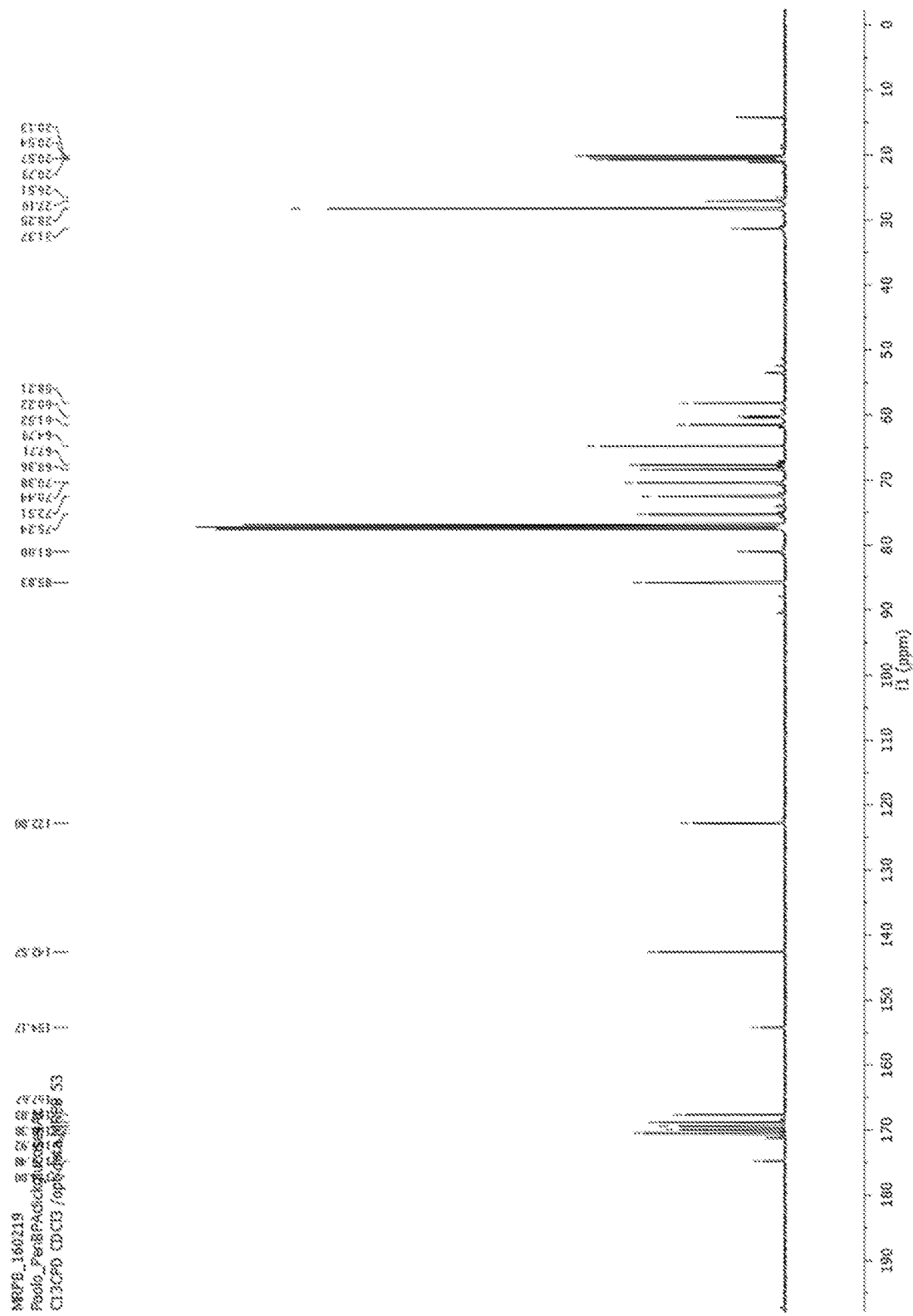
Figure 11:
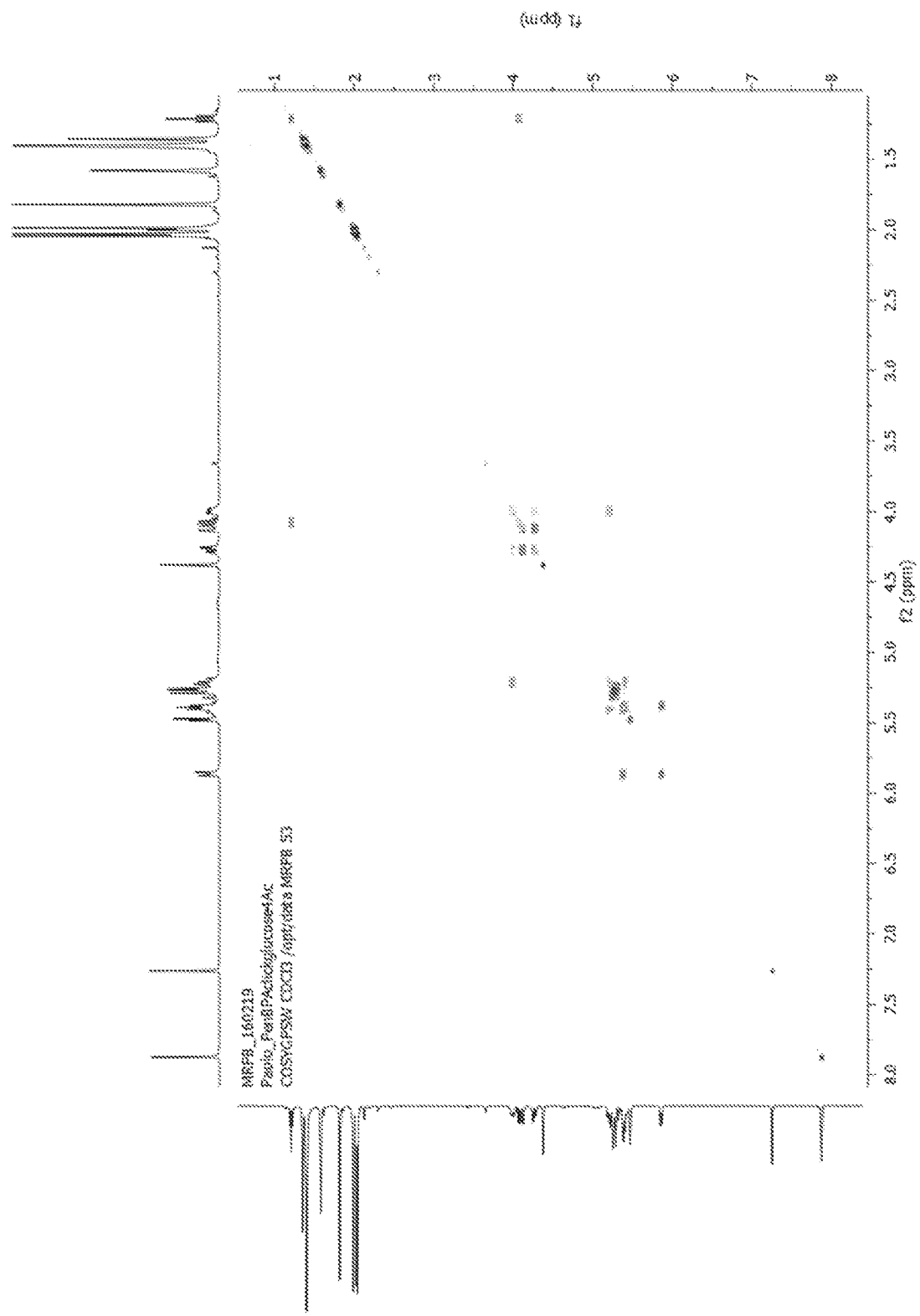
Figure 12:
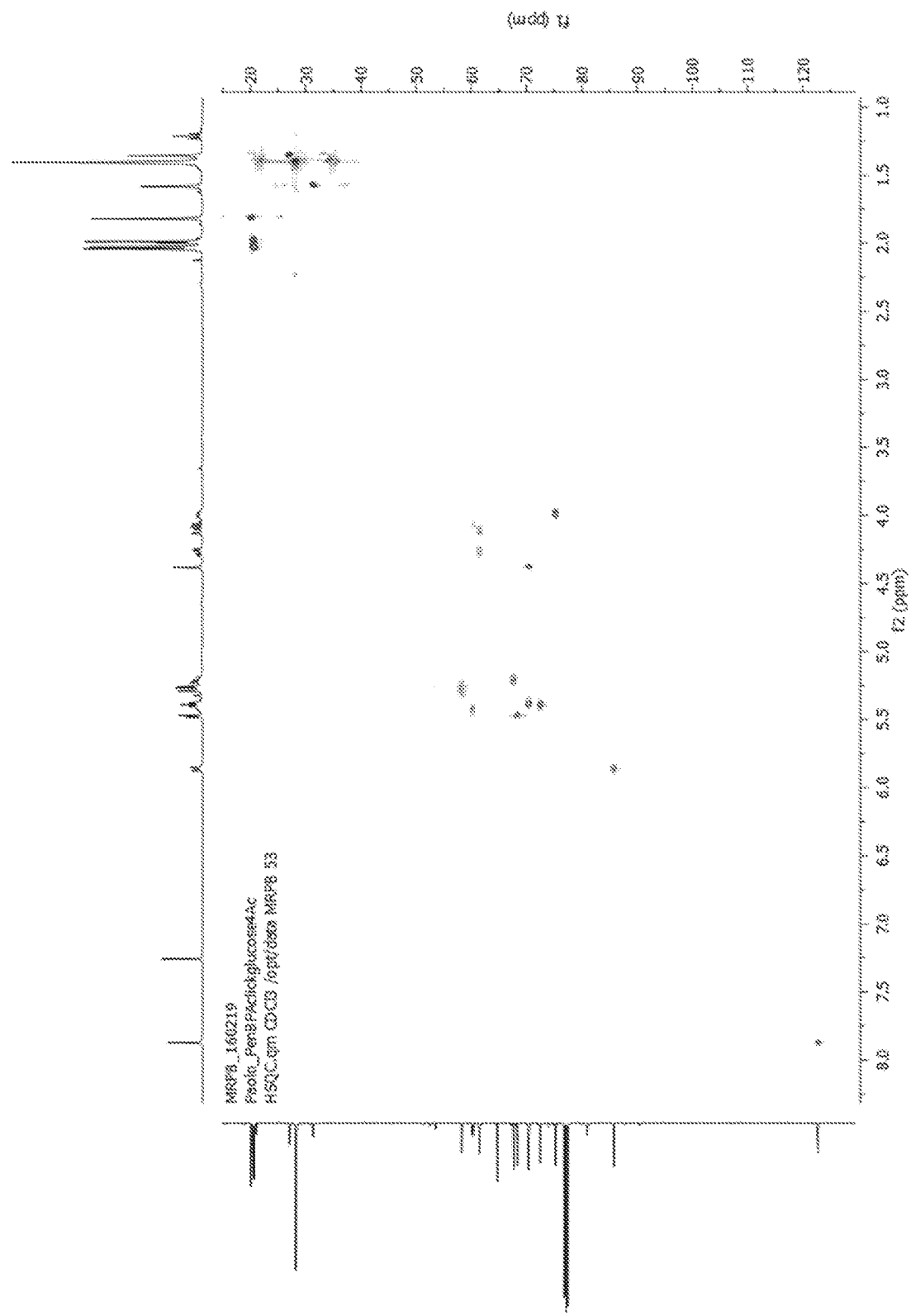
Figure 13:
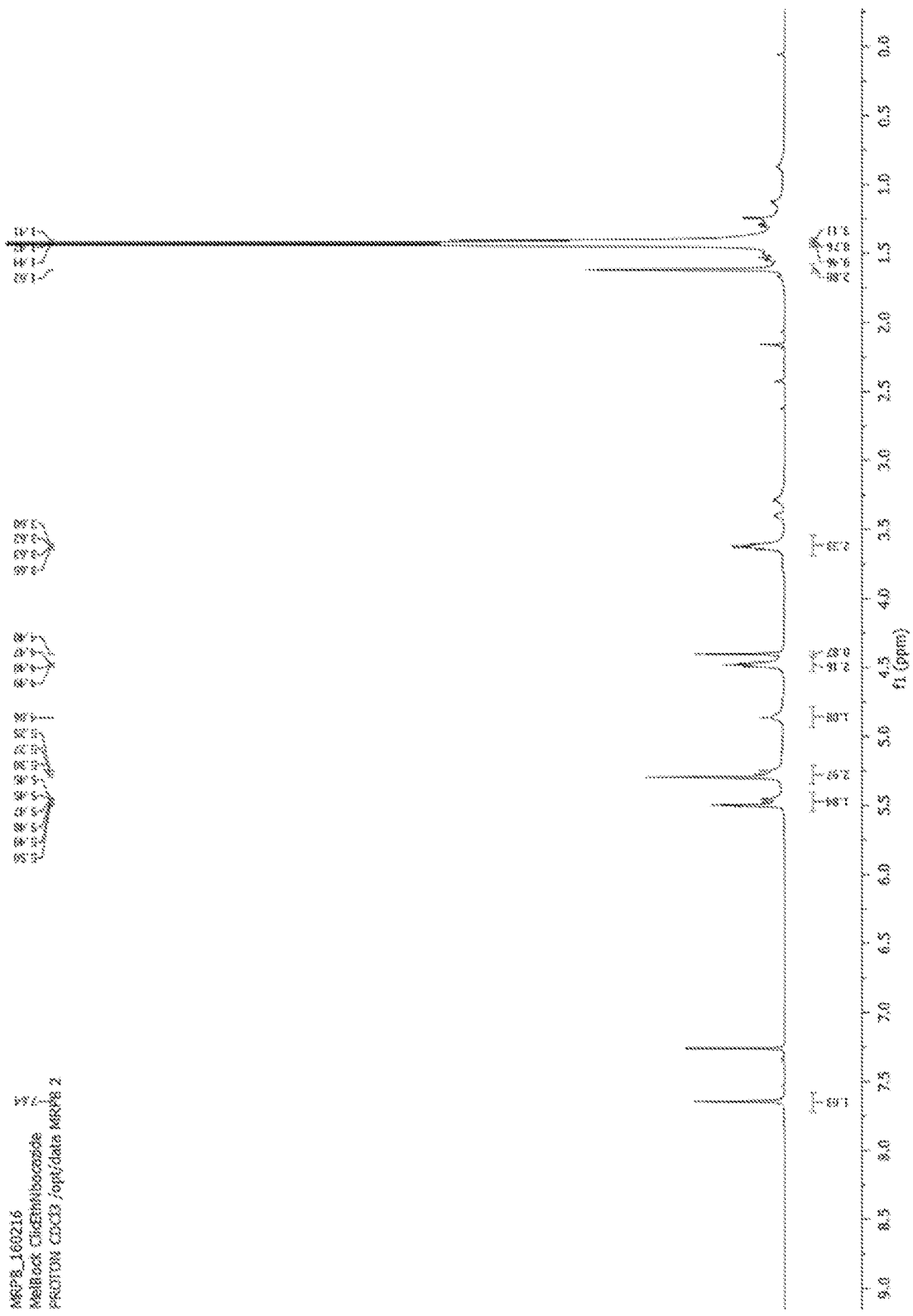
Figure 14:
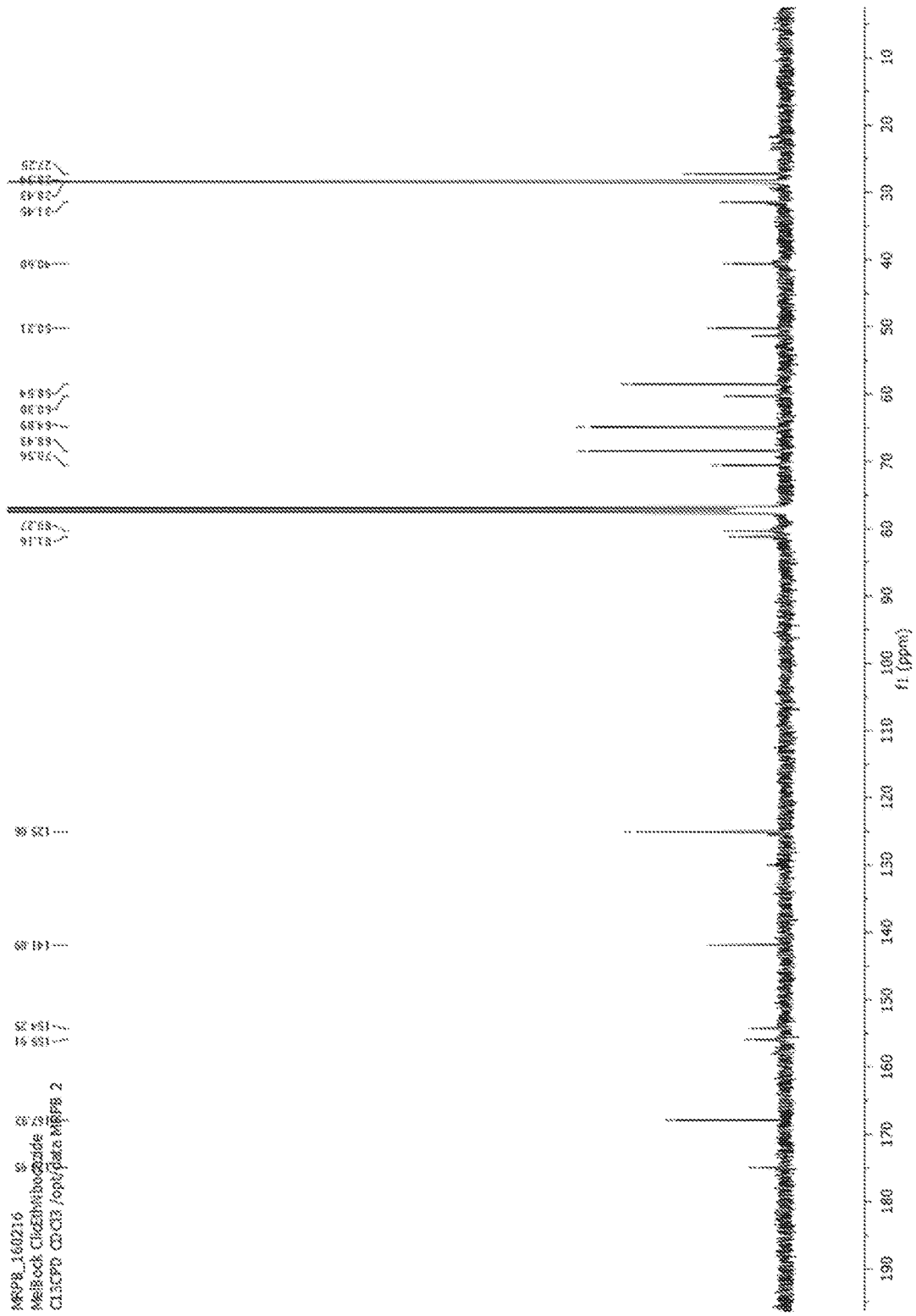
Figure 15:
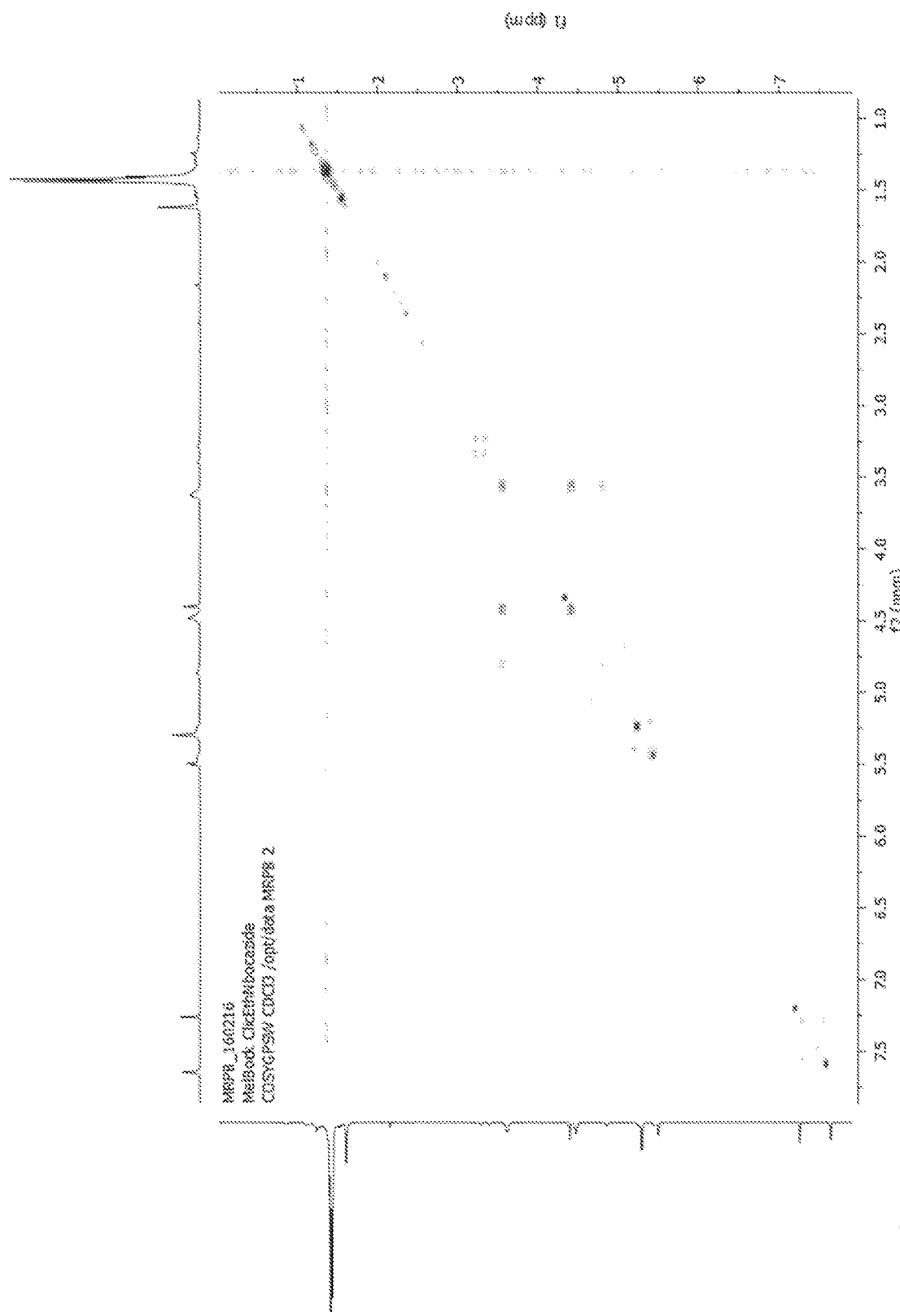
Figure 16:
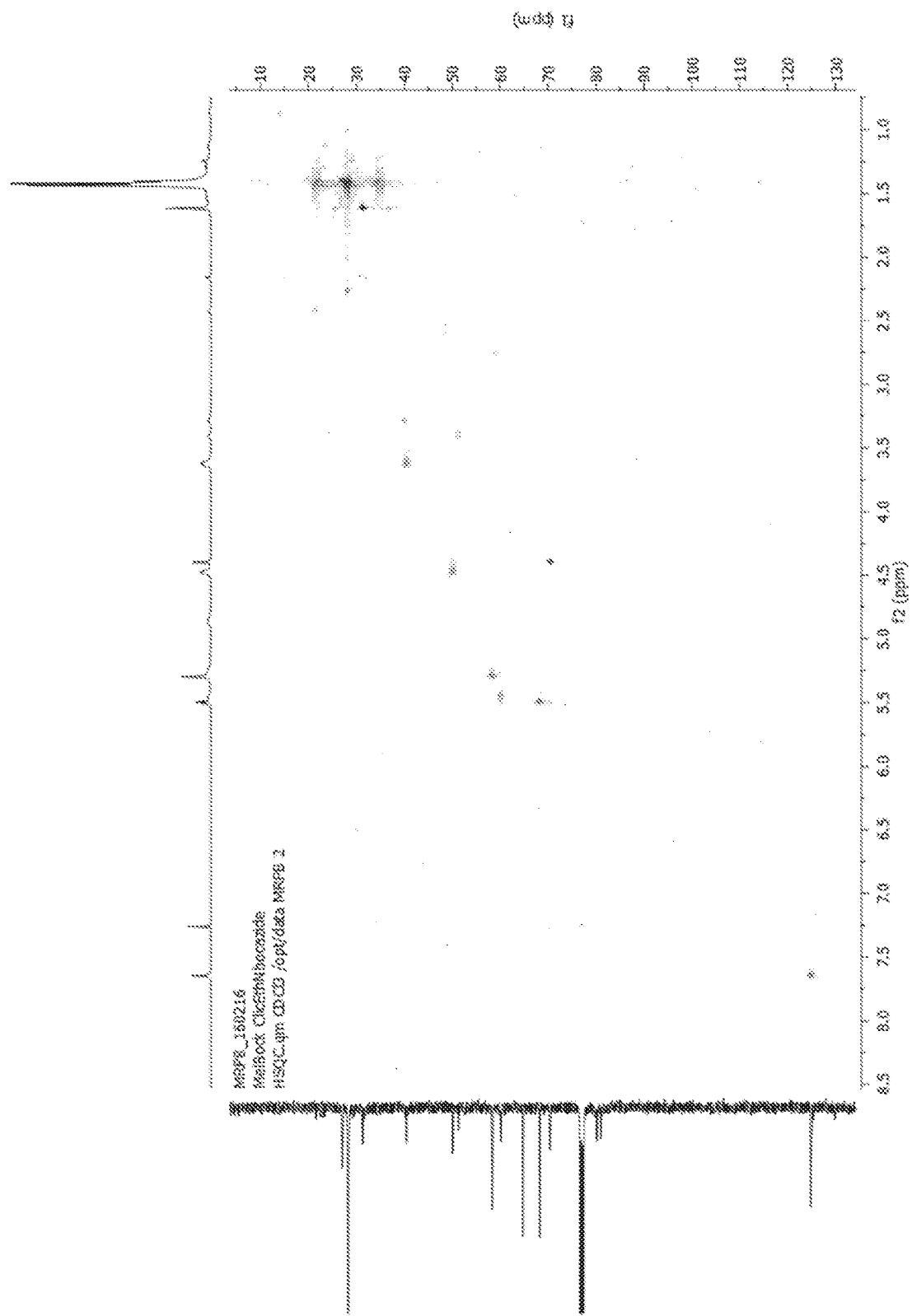

SYNTHESIS PROCESS OF PRECURSORS OF DERIVATIVES OF BETA-LACTAM NUCLEI AND PRECURSORS AND DERIVATIVES THEREOF

The present invention relates to a new synthesis process of precursors of derivatives of β-lactam nuclei.

The present invention also relates to a synthesis process of β-lactam nuclei containing triazoles variably functionalized starting from said precursors, the relative precursors and derivatives.

Resistance to antibiotics on the part of bacteria and fungi is a growing problem and is certainly one of the most important challenges to be faced in the years ahead. The indiscriminate use of antibiotics, in fact, especially in the past, has led to the formation of new bacteria resistant not only to a specific antibiotic, but also to different classes of antibiotics.[1]

The possibility of chemically modifying β-lactam nuclei is therefore extremely important for synthesizing new compounds having an antibiotic activity, i.e. capable of opposing these new or modified multi-resistant bacteria.[2]

The antibiotic activity of β-lactam derivatives is historically and scientifically associated with the chemical reactivity of the β-lactam ring, but it also varies in relation to the substituents present on said ring, in particular in relation to the substituents of the amine group.

It is known, however, that the nature of the substituents in position C-3 and C-4 also affects the biological activity of the β-lactam ring.[3]

Bicyclic antibiotics, such as Penicillins and Cephalosporins, are in fact composed of a β-lactam ring condensed with a thiazolidine ring having 5 or 6 atoms, with all the protons in a cis relationship with each other. The structural stress due to the fusion of the two cycles is extremely important for the reactivity of these antibiotics. An amide group in position 6 or 7 and a carboxylic group in position 2, are also present. In particular, the activity of the penicillins greatly depends on the substituents in position 6, whereas the carboxylic group is important for making modifications to the molecule and generating pro-drugs.

With respect to the relationship between structure and activity of penicillins, the most important features are therefore:
- the cis relation between the protons in position 5 and 6 on the beta-lactam ring;
- the bicyclic structure;
- the carboxylic group in position 2;
- the substituents of the amine group in position 6.

Hydrophobic substituent groups generally tend to increase the activity of penicillin towards Gram+ bacteria, whereas hydrophilic substituents increase the activity towards Gram− bacteria.

The attachment of a substituent group on the carboxyl group allows, for example, pro-drugs such as Bacampicillin[6] to be generated.

β-lactam antibiotics generally have a free carboxyl and negatively charged substituents, however, the diffusion of bacterial strains resistant to many of these antibiotics, as already mentioned, has led to the necessity of finding synthesis routes and precursors or derivatives of β-lactam compounds having suitable structural characteristics that allow them to be used as a starting point for generating new drugs, and also for identifying the relationships between these compounds and bacterial enzymes.

In addition to the antibacterial activity indicated above, β-lactam derivatives are in fact characterized by also having other biologically interesting properties: they act, in fact, as inhibitors of cholesterol absorption, as specific antigens when combined with proteins and are also synthons for the preparation of anti-cancer compounds such as Taxol.

Finally, for some β-lactam derivatives, a direct activity in the treatment of cancer has also been demonstrated.[4]

In general, the preparation of β-lactam derivatives follows some basis synthesis strategies:

the chemical synthesis that is exerted through the Staudinger reaction: a [2+2] cyclo-addition, of a ketene with an imme[5 a-b];

the chemo-enzymatic synthesis mediated by Penicillin G. Acylasis (PGA) from *E. Coli*, which is mainly concentrated on the acetylation of the amine group[6];

biosynthesis mediated by enzymes such as Isopenicillin N Synthase (IPNS)[7];

synthesis in solid phase with the introduction of triazoles groups in position 2, with a loss however in the carboxylic functionality. In particular, a library of aminoacyl triazolyl (peptidyl) penicillins has been produced and the antineoplastic activity studied[8]; these derivatives were obtained through a "click reaction" mediated by copper I, where, however, the azide was introduced with a reduction of the carbonyl according to the reaction scheme provided hereunder:

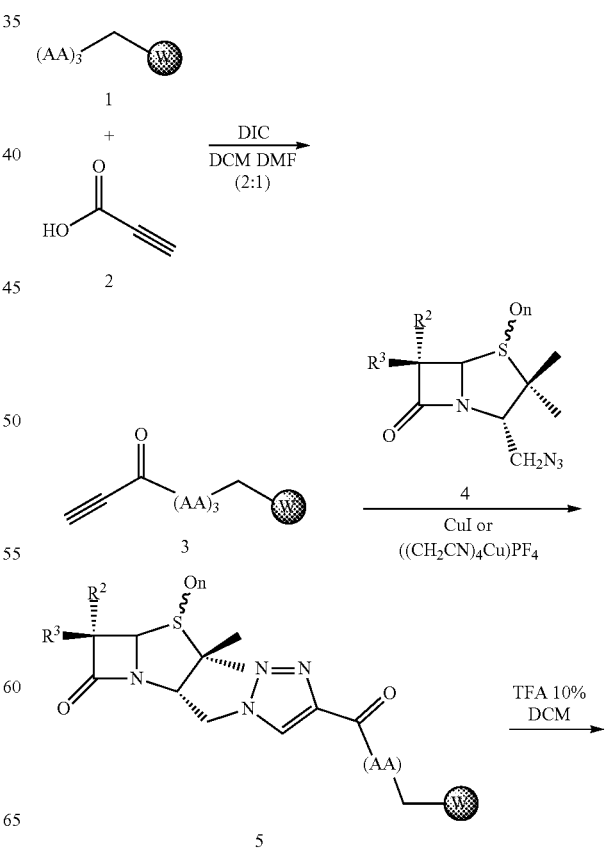

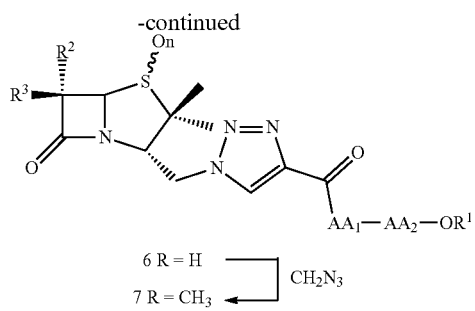

6 R = H
7 R = CH$_3$     CH$_2$N$_3$

AA = amino acid
I = 1.2

Very few functionalization examples of the carboxyl group in position 2 are provided in literature. In particular, the esterification of the carboxyl group in position 2 of these β-lactam nuclei was described in the art with the exclusive aim of protecting the carboxyl group itself[4-9].

Currently, therefore, the search for new antibacterial drugs is of vital importance and the possibility of synthesizing new non-traditional molecules allows new therapeutic agents to be conceived and obtained[15].

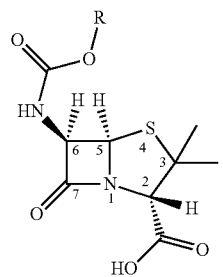

The objective of the present invention is to find an alternative synthesis route of precursors of β-lactam nuclei which can be carried out under extremely bland conditions that guarantee the stability of the β-lactam ring and allow a precursor of β-lactam derivatives to be obtained, wherein the β-lactam ring maintains its amine and carboxyl functionalities, introducing a group that allows a great versatility in the subsequent reactivity of the precursor.

The object of the present invention therefore relates to a synthesis process of precursors of derivatives of β-lactam compounds, said β-lactam compounds being selected from 6-aminopenicillanic acid and 7-aminocephalosporanic acid, which comprises the following steps:

a) protection of the amino group of the β-lactam compound, selected from 6-aminopenicillanic acid and 7-aminocephalosporanic acid, preferably 6-aminopenicillanic acid, by the formation of a carbamate through reaction with a dicarbonate;

b) esterification of the carboxyl group in position 2 of the β-lactam compound obtained in step a) by reaction with propargyl alcohol.

A further object of the present invention relates to a synthesis process of triazole derivatives of β-lactam compounds, wherein the precursor obtained at the end of step b) is subjected to a further step c):

c) cyclo-addition reaction between the precursor obtained in step b) and an organic azide with the formation of the corresponding triazole derivative of the β-lactam compound.

The β-lactam compound which is derivatized by the process according to the present invention is preferably 6-aminopenicillanic acid.

The process according to the present invention allows the esterification of the carboxyl group in position 2 of the β-lactam compound under mild conditions which do not cause the breakage of the β-lactam ring.

Step a) of the process of the present invention, which provides for the protection of the amine group through the formation of a carbamate, is carried out by reaction with a dicarbonate, which can be an alkyl, aromatic or cyclic dicarbonate. These dicarbonates can be possibly functionalized with groups having their own biological activity or which allow a further derivatization in said position 6 or 7, possibly to confer a different pharmacological activity[10a,b].

Examples of possible dicarbonates are the following: di-tert-butyl dicarbonate, bis(oxyran-2-ylmethyl) dicarbonate, bis(trifluoromethyl)dicarbonate, bis (2-ethoxycyclohexyl) dicarbonate or dibenzyl dicarbonate:

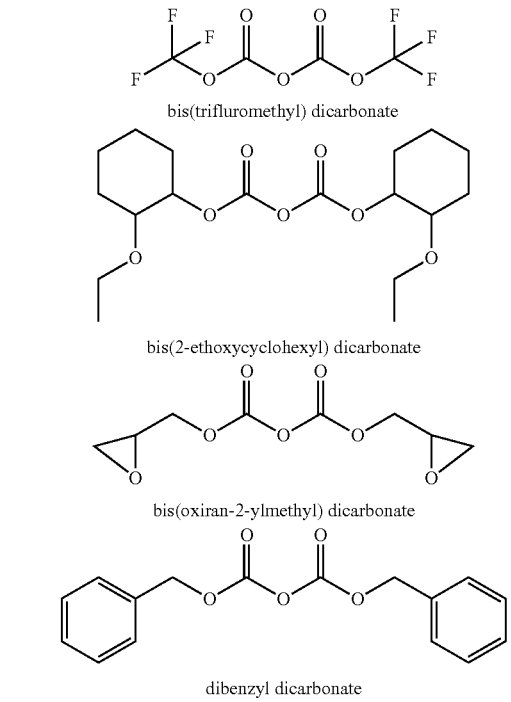

Bis(trifluoromethyl)dicarbonate[12], for example, can have a functionality with a biological activity, whereas ethyl carbonate has proved to have antineoplastic activities[11].

Step a) is preferably carried out by the formation of the carbamate with di-tert-butyl dicarbonate.

More specifically, step a) of the process according to the present invention is carried out at room temperature for a time ranging from 10 to 32 hours, preferably equal to about 24 hours, in a solvent consisting of a 1:1 mixture by volume of 1,4-dioxane and water, or a 1:1 mixture by volume of THF and water.

The reagent di(tert-butyl-dicarbonate) is present in a molar ratio ranging from 2 to 1, preferably in a molar ratio ranging from 1.3 to 1, with respect to the β-lactam compound.

Step b) is carried out under anhydrous conditions using an anhydrous solvent selected from diethyl ether, 1,4-dioxane, THF or diethyl ether, 1,4-dioxane, THF in a ratio of 4/1 with chloroform or DCM, in the presence of an anhydrous amine selected from triethyl amine (anhydrified on molecular sieves) and dimethylamino-pyridine.

The reaction of step b) is carried out at room temperature for a time ranging from 24 to 52 hours, preferably from 24 to 36 hours.

The derivative esterified with the propargyl group in position 2 of the β-lactam nucleus, obtained at the end of step b), allows a "copper(I)-catalyzed azide-alkyne cycloaddition (CuAAC) reaction" to be carried out with the consequent introduction of various suitable and selected organic azides.

Step c) of the synthesis process of triazole derivatives according to the present invention, is a cycloaddition reaction, and, more specifically, is a dipolar 1,3-cycloaddition, wherein the organic azide is selected from tert-butyl 2-azidoethyltert-butylcarbamate, 2,3,4,6-tetra-O-acetyl-β-D-glucopy-ranosyl azide and 2,3,4,6-OH-β-D-glucopyranosyl azide. The cycloaddition reaction is mediated by copper in oxidation state I.

Step c) is carried out in a mixture of water and $C_1$-$C_4$ alkyl alcohol, preferably in water and isopropanol (IPA) 1:1 by volume at a temperature ranging from 55 to 60° C., preferably from 58 to 60° C., for a time ranging from 4 to 10 hours, preferably from 4.5 to 6 hours.

A further object of the present invention relates to triazole derivatives having the following structural formulae:

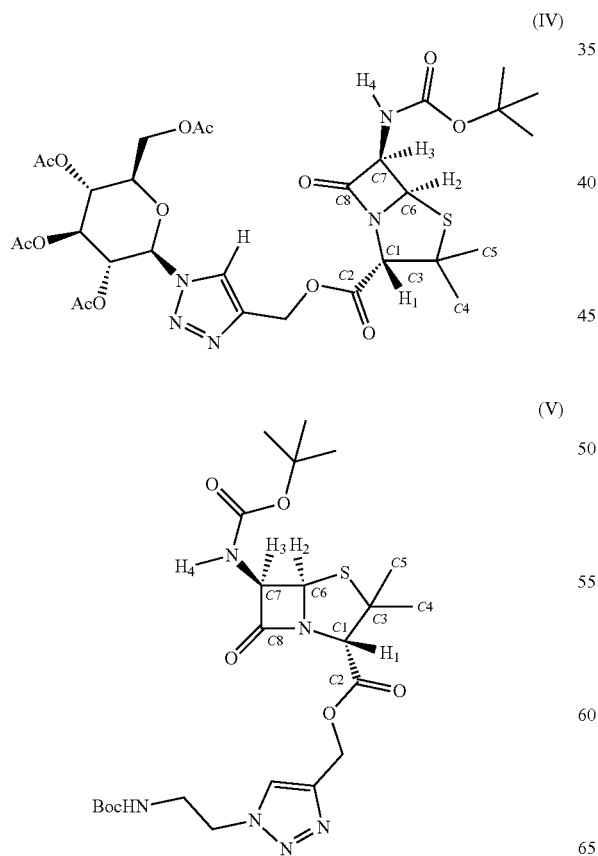

A further object of the present invention relates to the precursors obtained at the end of step b) having the following structural formulae

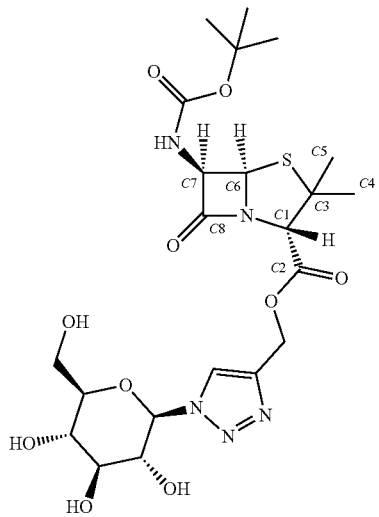

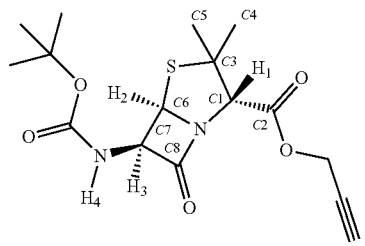

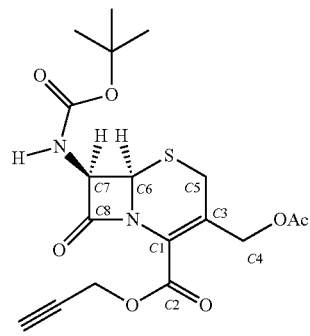

These intermediates or precursors can then be functionalized in very different ways by means of suitable reactions.

The precursors or intermediates having formula (III) or (IX) are particularly interesting as
  they are precursors of β-lactam derivatives in which the propargyl group has been inserted, maintaining the β-lactam ring intact, with the original functionalities: amine group in 6 or 7 and carboxyl group in 2;
  a propargyl group has been introduced, which can be easily modified; this functional group is, in fact, effective for generating compounds through a cycloaddition reaction having substituents of a varying nature and with a different polarity and hydrophilicity on the carboxyl in position 2;
  they allow the introduction of new functional groups for studying both a possible reduction in the activity of β-lactamase, and also for increasing or diversifying the action spectrum of new β-lactam derivatives;

they enable the introduction of mono- di- or oligo-carbohydrates in order to increase the biocompatibility of the drug, but also to selectively direct the drug itself towards a particular bacterial agent. It is known, in fact, that bacteria bind to the cell membrane of the host cell also through the recognition of specific carbohydrates;

they allow the synthesis of macrocycles containing beta-lactam rings in order to investigate a different activity of the beta-lactam nucleus. Whereas β-lactam antibiotics have a negative influence on the formation of the bacterial membrane, by binding to a specific enzyme of the same bacterium (greater extracellular activity), macrolides exert their antibacterial activity by binding to specific ribosomal (intracellular) units and blocking the protein synthesis;

they allow the synthesis of nanoparticles containing azide functionalities to be functionalized, through a 1,3 dipolar cyclization reaction with β-lactams, in order to examine their resistance to bacteria;

they allow the synthesis of new pro-drugs and new β-lactam derivatives having an anti-cancer activity;

the same amine group can be further transformed into dithiocarbamate. Dithiocarbamates are in fact recognized at a pharmacological level for their properties as chelating agents of metals, antimicrobials and fungicides.[13] This also guarantees the possibility of differentiating the activity spectrum of β-lactam derivatives.

What is specified above also shows the importance of the derivatives having formula (IV), (V) and (VI) which, also thanks to the presence of a triazole group having marked pharmacological activities, can be used as drugs. In addition to the β-lactam ring, these new compounds, in fact, have a triazole group having marked pharmacological activities. Triazoles are also known as fungicides (they inhibit the formation of ergosterol) and have chelating properties towards metals that are useful for the use of these compounds in the study of the antibacterial activity against β-lactamase Class B which are enzymes responsible for the degradation of most β-lactam antibiotics. In particular, the New Dheli Metallo-β-lactamase is an enzyme that uses zinc for deactivating the β-lactam rings[16]. Triazoles are recognized as substances capable of chelating zinc and inhibiting endoproteinases, enzymes involved in tissue remodeling[17].

Furthermore, the presence in the derivative (VI) of a group such as deprotected glucose increases the biocompatibility and absorption at a cellular level and even at the level of the central nervous system by passing through the blood-brain membrane.

The presence of glucose in the derivative (V) or (VI) (as also other carbohydrates), moreover, can be of help in selectively directing new therapeutic agents towards certain bacterial agents. As already specified, the bacteria adhere to the cell membranes of host cells after recognizing specific sugars present on the cell surface.

REFERENCES 1. http://www.who.int/mediacentre/factsheets/fs194/en/;
2. S. R. Smith, *J. Org. Chem.*, 2014, 79, 1626-1639;
3. N. Arya, *European Journal of Medicinal Chemistry*, 2014, 74, 619-656;
4. D. B., Boggian et al. *Med. Chem. Commun.*, 2015, 6, 619-625;
5. a) H. Staudinger, *Liebigs Ann. Chem.* 1907, 356, 51-123; b) C. Palomo et al., *Eur. J. Org. Chem.* 1999, 3223-3235;
6. P. Bonomi et al., *Molecules*, 2013, 18, 14349-14365;
7. N. I. Burzlaff et al, Nature, 1999, 401, 721-724;
8. P. G. Cornier, et al., *Med. Chem. Commun.*, 2014, 5, 214-218;
9. P. Ilankumaran et al., Che. Comm. Commun., 1996, 1967-1958];
10. a) Trillion Science Inc. Patent: US2009/181165 A1, 2009 b) EISAI CO., LTD. Patent: WO2003/99195 A2, 2003; Pagg. 60-61;
11. K. J. Field, C. M. Lang, *Laboratory Animals*, 1998, 22, 255-262;
12. P. Garcia et al., Journal of Fluorine Chemistry, 2005, 126, 984-990;
13. Nand Lal, *Chemistry & Biology Interface*, 2014, 4, 6, 321-340;
14. http://pharmafactz.com/medicinal-chemistry-of-beta-lactam-antibiotics/;
15. M. I. Konaklieva, Antibiotics 2014, 3, 128-142;
16. M. Zheng et al., J. Phys. Chem. B 2013, 117, 11596-11607;
17. M. Hu et al., Org. Lett., 2008, 10, 24, 5529-5531.

The following examples are representative of the present invention, without limiting its scope in any way.

EXAMPLE 1

Synthesis of (2S,5R,6R)-6-(tert-butoxycarbonyl amino)-3,3-dimethyl-7-oxo-4-thio-1-azabicyclo[3.2.0]heptane-2-carboxylic Acid

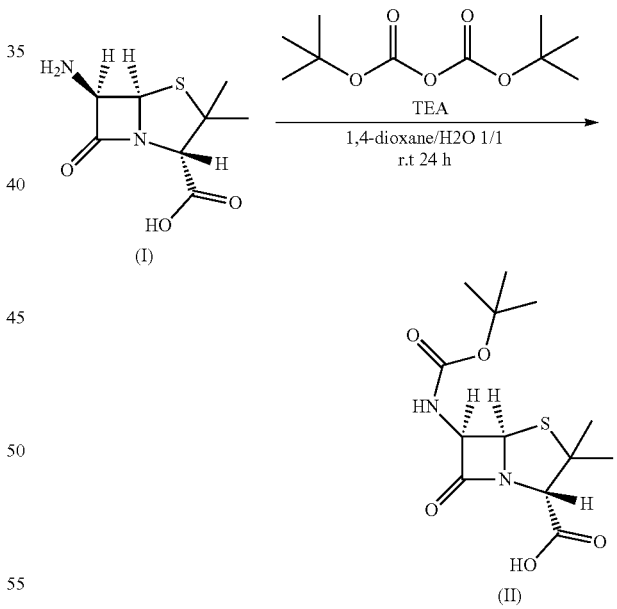

1 g (4.624 mmoles) of 6-APA was suspended, in a 100 ml flask, in 30 ml of a solution of water and dioxane in a ratio of 1:1 by volume, at room temperature. After the addition of 1.288 ml (9.248 mmoles) of TEA, a complete solubilization was obtained. 1.312 g of di-tert-butyl dicarbonate (6.0112 mmoles) where then added to this solution and the solution was kept under stirring at room temperature for 24 hours.

The reaction trend was monitored by means of thin layer chromatography (TLC) with hexane/acetone 1:1 as solvent and when the starting reagent had been totally consumed, the dioxane was removed by means of evaporation at reduced pressure.

The compound thus obtained was extracted using DCM (3×50 ml) and the organic phase was dried on NaSO$_4$. The organic solvent was then removed under vacuum obtaining a white foam with a yield of 90%.

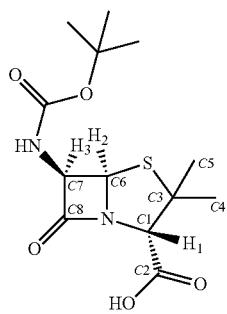

(II)

$^1$H-NMR (400 MHz, CDCl$_3$): δ 5.51 (d, J=4.2 Hz, H2-β-lactam, 1H), 5.35 (dd, J=9.9, 3.7 Hz, H3-β-lactam, 1H), 5.28 (d, J=9.6 Hz, H4-β-lactam, 1H), 4.27 (br s, H1-β-lactam, 1H), 1.61 (s, 3H), 1.56 (s, 3H), 1.40 (s, 9H).

$^{13}$C-NMR (100 MHz, CDCl3): δ 174.99 (s, 1C, —NC═O, C$_8$β-lactam), 172.98 (s, 1C, —OC═O, C$_2$β-lactam), 154.37 (s, 1C, C═O Boc), 80.63 (s, 1C, —C(CH$_3$)$_3$), 73.11 (s, 1C, C$_1$β-lactam), 67.96 (s, 1C, C$_7$β-lactam), 64.68 (s, 1C, C$_3$β-lactam), 59.71 (s, 1C, C$_6$β-lactam), 32.15 (s, 1C, CH$_3$, C$_4$β-lactam), 28.29 (s, 1C, CH$_3$ C$_5$β-lactam), 27.60 (s, 3C, —C(CH$_3$)$_3$)

Melting point: 74-76° C.

Chemical Formula: C$_{13}$H$_{20}$N$_2$O$_5$S

Molecular Weight: 316.37

The $^1$H-NMR $^{13}$C-NMR spectra of the compound having formula (II) are indicated in FIGS. 1-4.

EXAMPLE 2

Synthesis of (2S,5R,6R)-prop-2-inyl 6-(tert-butoxycarbonylamino)-3,3-dimethyl-7-oxo-4-thio-1-azabicyclo-[3.2.0]heptane-2-carboxylate

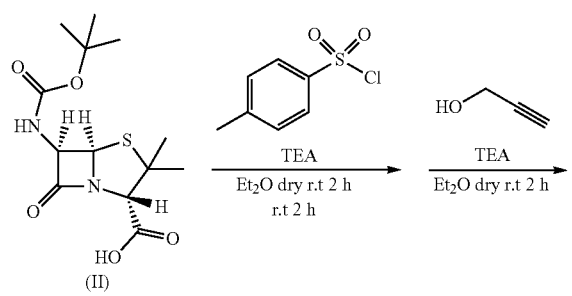

(II)

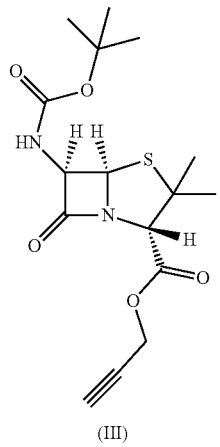

(III)

316.37 mg of (2S,5R,6R)-6-(tert-butoxycarbonyl amino)-3,3-dimethyl-7-oxo-4-thio-1-azabicyclo[3.2.0]-heptane-2-carboxylic acid (1 mmole) and 139 µl (1 mmole) of anhydrous TEA (alternatively 175 µL of DIPEA can be used (N,N diisopropyl-ethyl amine)) were dissolved in 10 ml of anhydrous Et$_2$O/anhydrous DCM (CH$_2$Cl$_2$) 8/1 (alternatively only DCM, dioxane or THF can be used) at room temperature under an atmosphere of N$_2$. 190.65 mg (1 mmole) of para-toluenesulfonyl chloride (alternatively 98 µL of methanesulfonyl chloride or 144 µL of Diethylphosphate chloride can be used) were added to the solution which was then left under stirring at room temperature for 2 hours. The formation of a white solid (if the reaction is carried out in ether) indicates the formation of triethylamine hydrochloride (or DIPEA).

A solution composed of 57.70 ml (1 mmole) of propargyl alcohol and 139 ml (1 mmole) of anhydrous TEA (or alternatively 175 µL of DIPEA) was prepared in 3 ml of anhydrous Et$_2$O (or DCM) and was added to the mixture in a single portion at room temperature. The suspension thus obtained was left under stirring in an inert atmosphere for 48 hours.

The reaction trend was monitored by means of thin layer chromatography (TLC) with hexane/AcOEt 4:1 as solvent (Rf=0.25) and when the starting reagent had been totally consumed, 10 ml of water were added to the reaction mixture, the compound thus obtained was extracted using diethyl ether (3×15 ml) and the organic phase was dried on NaSO$_4$. The sticky oil, red-coloured when the activator used is para-toluenesulfonyl chloride or methanesulfonyl chloride, or greenish when the activator used is diethyl phosphate chloride, was purified by means of flash chromatography, obtaining 110 mg of a pale yellow-coloured oil (35% yield).

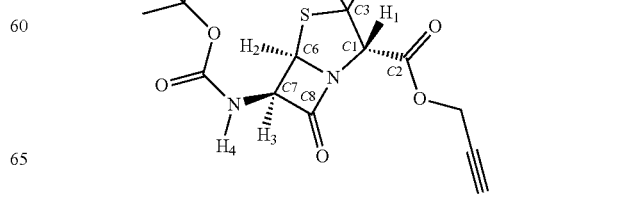

(III)

¹H-NMR (400 MHz, CDCl₃): δ 5.51 (d, J=4.2 Hz, 1H, H2 β-lactam), 5.46 (dd, J=8.7, 3.2 Hz, 1H, H3 β-lactam), 5.29 (d, J=9.1 Hz, 1H, H4 β-lactam), 4.79 (dd, J=15.5, 2.5 Hz, 1H, CH₂), 4.69 (dd, J=15.5, 2.4 Hz, 1H, CH₂), 4.41 (br s, 1H, H1 β-lactam), 2.51 (t, J=2.5 Hz, 1H, ≡CH), 1.64 (s, 3H), 1.51 (s, 3H), 1.42 (s, 9H).

¹³C-NMR (100 MHz, CDCl3): δ 174.97 (s, 1C, —NC=O, C₈β-lactam), 167.26 (s, 1C, —OC=O, C₂β-lactam), 154.24 (s, 1C, C=O Boc), 81.16 (s, 1C, —C(CH₃)₃), 76.67 (s, 1C, HC≡C—), 70.62 (s, 1C, HC≡C—), 70.46 (s, 1C, —CH—COOR, C₁β-lactam), 68.45 (s, 1C, BocNHC—CH—S—, C₇β-lactam), 65.04 (s, 1C, —C(CH3)₂, C₃β-lactam), 60.28 (s, 1C, —CH—NHBoc, C₆β-lactam), 52.92 (s, 1C, HC≡C—CH₂—), 31.39 (s, 1C, CH₃C₄β-lactam), 28.33 (s, 1C, CH₃, C₅β-lactam), 27.30 (s, 3C, —C(CH₃)₃)

Chemical Formula: C₁₆H₂₂N₂O₅S

Molecular Weight: 354.42

The ¹H-NMR ¹³C-NMR spectra of the compound having formula (III) are indicated in FIGS. 5-8.

EXAMPLE 3

Synthesis of (2R,3R,4S,5R,6R)-2-(acetoxymethyl)-6-(4-(((2S,5R,6R)-6-(tert-butoxycarbonylamino)-3,3-dimethyl-7-oxo-4-thio-1-azabicyclo[3.2.0]heptane-2-carbonyl-oxy)methyl-1H-1,2,3-triazol-1-yl) tetrahydro-2H-pyran-3,4,5-triyl triacetate

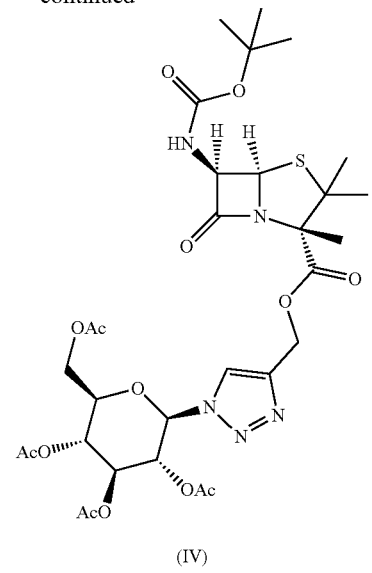

(IV)

200 mg (0.564 mmoles) of (2S,5R,6R)-prop-2-inyl 6-(tert-butoxycarbonylamino)-3,3-dimethyl-7-oxo-4-thio-1-azabicyclo[3.2.0]heptane-2-carboxylate (1), 232 mg of 2,3,4,6-tetra-O-acetyl-β-D-glucopyranosyl azide (0.620 mmoles), 7.72 mg of CuSO₄ 5H₂O (0.031 mmoles) and 61.38 mg (0.31 mmoles) of sodium ascorbate were suspended in 10 ml of a solution of water and isopropyl alcohol 1:1. The reaction mixture was left under stirring at 60° C. for 4 hours and the reaction trend was monitored by means of thin layer chromatography (TLC) with DCM/Et₂O 9:1 as solvent (Rf=0.7). When the starting reagent had been totally consumed, the alcohol was removed at reduced pressure and the compound was extracted with DCM (3×15 ml), the organic phase was dried on NaSO₄ giving a pale brown solid which was purified by means of flash chromatography using DCM/Et₂O 9.5:0.5 as solvent, obtaining 120 mg of a white solid (0.165 mmoles) (30% yield).

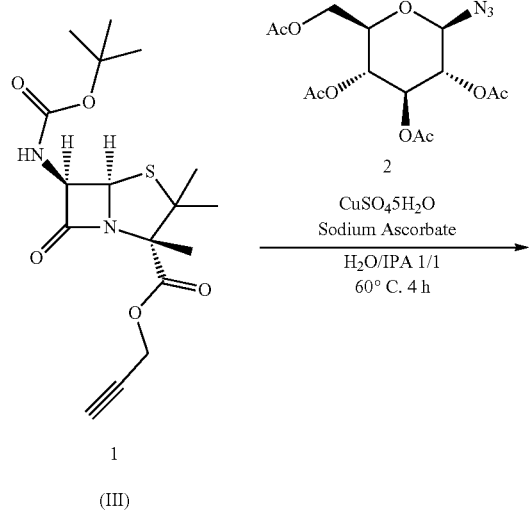

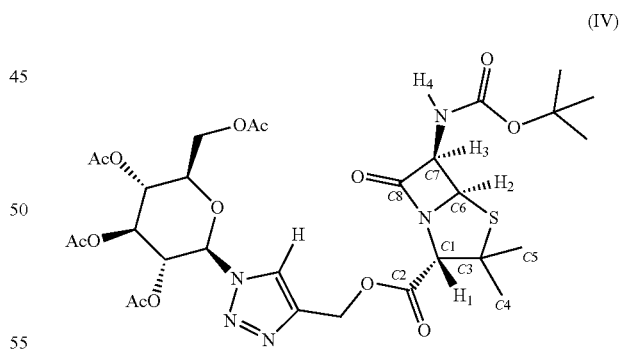

(IV)

¹H-NMR (400 MHz, CDCl3): δ 7.89 (s, 1H, H-triazole), 5.86 (d, J=9.1 Hz, 1H, H1-glu), 5.48 5.48 (d, J=4.2 Hz, 1H, H2 β-lactam), 5.43 (d, J=9.7 Hz, 1H H3 β-lactam) 5.42-5.39 (m, 2H, H3-H2 glu), 5.32-519 (m, 4H, CH₂-tryazole H2 β-lactam, H4 glu), 4.38 (s, 1H, H1 β-lactam), 4.27 (dd, J=12.7, 4.9 Hz, 1H, H6 glu), 4.12 (dd, J=12.6, 2.0 Hz, 1H, H6 glu), 3.99 (ddd, J=10.1, 4.9, 2.1 Hz, 1H, H5 glu), 2.04 (s, 3H, CH₃C=O), 2.03 (s, 3H, CH₃C=O), 1.99 (s, 3H, CH₃C=O), 1.82 (s, 3H, CH₃C=O), 1.58 (s, 3H, CH₃ β-lactam), 1.40 (s, 9H, C(CH₃)₃), 1.36 (s, 3H, CH₃ β-lactam), $^{13}$C-NMR (100 MHz, CDCl3): δ 174.97 (s, 1C, —NC=O, C$_8$β-lactam), 170.57, (s, 1C, CH$_3$C=O), 170.00 (s, 1C, CH$_3$C=O), 169.44 (s, 1C, CH$_3$C=O), 168.90 (s, 1C, CH$_3$C=O), 167.73 (s, 1C, —OC=O, C$_2$β-lactam), 154.24 (s, 1C, C=O Boc), 142.61 (s, 1C, C$_4$-triazole), 122.85 (s, 1C, C$_5$-triazole), 85.90 (s, 1C, C$_1$Glu), 81.16 (s, 1C, —C(CH$_3$)$_3$), 75.31 (s, 1C, C$_5$Glu), 72.53 (s, 1C, C$_2$Glu), 70.49 (s, 1C, C$_1$β-lactam), 70.38 (s, 1C, C$_3$Glu), 68.38 (s, 1C, C$_7$β-lactam), 67.69 (s, 1C, C$_4$Glu), 64.84 (s, 1C, C$_3$β-lactam), 61.53 (s, 1C, C$_7$Glu), 60.21 (s, 1C, C$_6$β-lactam), 58.25 (s, 1C, —CH$_2$-triazole) 31.36 (s, 1C, C$_4$β-lactam), 28.30 (s, 3C, —C(CH$_3$)$_3$), 27.16 (s, 1C, C$_5$β-lactam), 20.80 (s, 1C, CH$_3$C=O), 20.64 (s, 1C, CH$_3$C=O), 20.61 (s, 1C, CH$_3$C=O), 20.21 (s, 1C, CH$_3$C=O)

Chemical Formula: C$_{30}$H$_{41}$N$_5$O$_{14}$S
Molecular Weight: 727.74
Melting Point: 147° C.

The $^1$H-NMR $^{13}$C-NMR spectra of the compound having formula (IV) are indicated in FIGS. 9-12.

EXAMPLE 4

Synthesis of 2S,5R,6R)-6-(tert-butoxycarbonylamino)-ethyl)-1H-1,2,3-triazol-4-yl)methyl 6-(tert-butoxy-carbonylamino) 3,3-dimethyl-7-oxo-4-thio-1-azabicyclo-[3.2.0]heptane-2-carboxylate

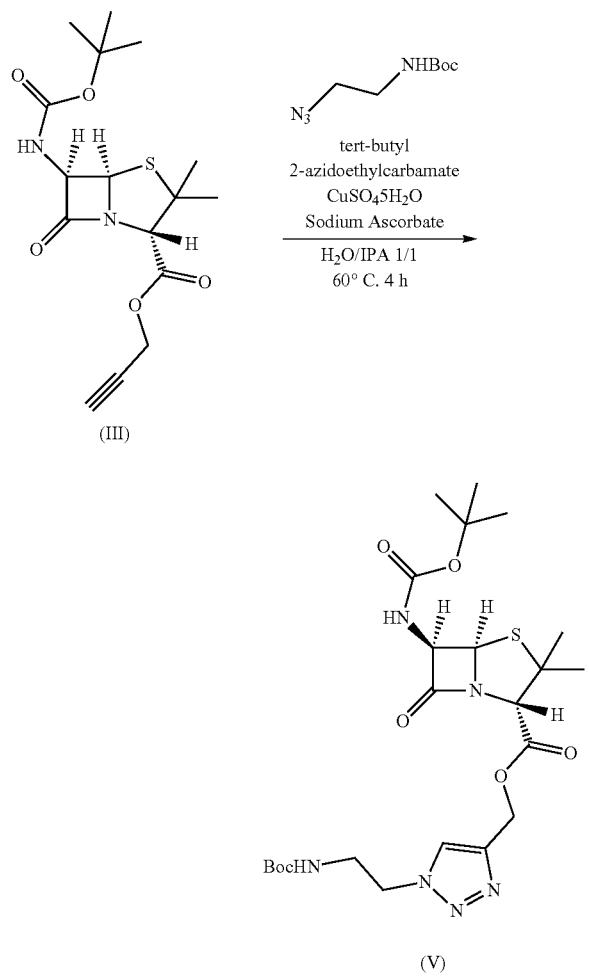

150 mg (0.4232 mmoles) of (2S,5R,6R)-prop-2-inyl 6-(tert-butoxycarbonylamino)-3,3-dimethyl-7-oxo-4-thio-1-azabicyclo[3.2.0]heptane-2-carboxylate (1), 94.57 mg of tert-butyl 2-azidoethylcarbamate (0.5078 mmoles), 6.33 mg of CuSO$_4$ 5H$_2$O (0.0254 mmoles) and 50.30 mg (0.254 mmoles) of L(+)sodium ascorbate were suspended in 10 ml of a solution of water and isopropyl alcohol 1:1. The reaction mixture was left under stirring at 60° C. for 4 hours and the reaction trend was monitored by means of thin layer chromatography (TLC) with DCM/Et$_2$O 9.5:0.5 as solvent (Rf=0.7). When the starting reagent had been totally consumed, the alcohol was removed at reduced pressure and the compound was extracted with DCM (3×15 ml), the organic phase was dried on NaSO$_4$ giving a brownish solid which was purified by means of flash chromatography using DCM/Et$_2$O 9.5:0.5 as solvent, obtaining 90 mg of a pale brown foam (40% yield).

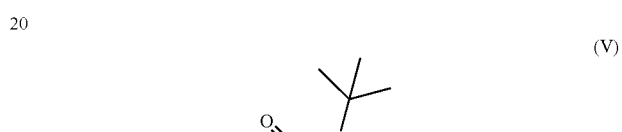

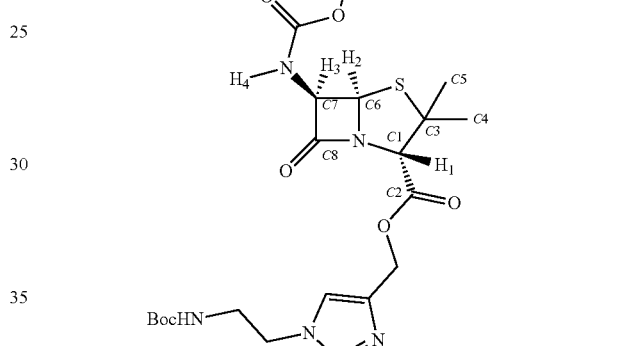

$^1$H-NMR (400 MHz, CDCl3) δ 7.65, (s, 1H, H-triazole), 5.50 (d, J=4.2 Hz, 1H, H2 β-lactam), 5.47 (dd, J=9.4, 4.0 Hz, 1H, H3 β-lactam), 5.30 (s, 2H, CH$_2$-tryazole), 5.27 (d, J=9.9 Hz, 1H, H4 β-lactam), 4.87 (s, 1H, Boc-NH—CH$_2$), 4.48 (t, J=5.6 Hz, 2H, Boc-NH—CH$_2$), 4.40 (s, 1H, H1 β-lactam), 3.63 (m, 2H, Boc-NH CH$_2$—CH$_2$—), 1.62 (s, 3H, CH$_3$ β-lactam), 1.44 (s, 9H, C(CH$_3$)$_3$), 1.42 (s, 9H, C(CH$_3$)$_3$), 1.40 (s, 3H, CH$_3$ β-lactam)

$^{13}$C-NMR (100 MHz, CDCl3) δ 174.99 (s, 1C, —NC=O, C$_8$β-lactam), 167.94 (s, 1C, —OC=O, C$_2$β-lactam), 155.93 (s, 1C, C=O Boc), 154.24 (s, 1C, C=O Boc), 141.88 (s, 1C, C$_4$-triazole), 125.09 (s, 1C, C$_5$-triazole), 81.17 (s, 1C, —C(CH$_3$)$_3$), 80.28 (s, 1C, —C(CH$_3$)$_3$), 70.56 (s, 1C, C$_1$β-lactam), 68.43 (s, 1C, C$_7$β-lactam), 64.84 (s, 1C, C$_3$β-lactam), 60.27 (s, 1C, C$_6$β-lactam), 58.48 (s, 1C, —CH$_2$-triazole) 50.20 (s, 1C, Boc-NH CH$_2$—CH$_2$—), 40.60 (s, 1C, Boc-NH CH$_2$—CH$_2$—), 31.43 (s, 1C, C$_4$β-lactam), 28.43 (s, 3C, —C(CH$_3$)$_3$), 28.33 (s, 3C, —C(CH$_3$)$_3$), 27.25 (s, 1C, C$_5$β-lactam), Chemical Formula: C$_{23}$H$_{36}$N$_6$O$_7$S
Molecular Weight: 540.63
Melting Point: 78-83° C.

The $^1$H-NMR $^{13}$C-NMR spectra of the compound having formula (V) are indicated in FIGS. 13-16.

EXAMPLE 5

Synthesis of (2S,5R,6R)-(1-((2R,3R,4S,5S,6R)-3,4,5-trihydroxy-6-(hydroxymethyl)tetrahydro-2H-pyran-2-yl)-1H-1,2,3-triazol-4-yl)methyl 6-(tert-butoxycarbonyl-amino)-3,3-dimethyl-7-oxo-4-thio-1-azabicyclo[3.2.0]-heptane-2-carboxylate

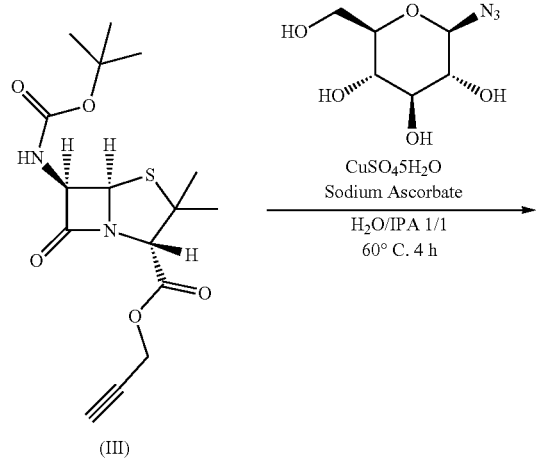

(III)

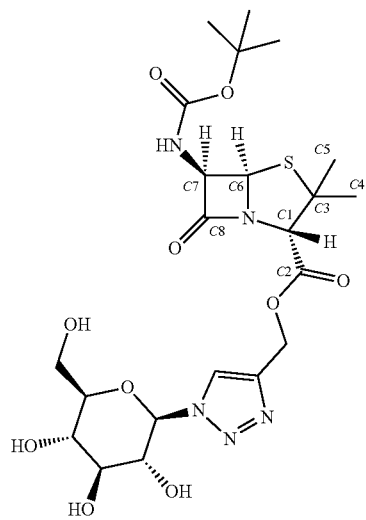

(VI)

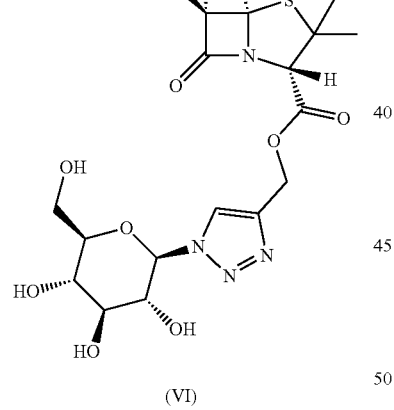

(VI)

200 mg (0.564 mmoles) of (2S,5R,6R)-prop-2-inyl 6-(tert-butoxycarbonylamino)-3,3-dimethyl-7-oxo-4-thio-1-azabicyclo[3.2.0]heptane-2-carboxylate (1), 127 mg of 2,3,4,6-tetra-O-acetyl-β-D-glucopyranosyl azide (0.620 mmoles), 7.72 mg of $CuSO_4$ $5H_2O$ (0.031 mmoles) and 61.38 mg (0.31 mmoles) of sodium ascorbate were suspended in 10 ml of a solution of water and isopropyl alcohol 1:1. The reaction mixture was left under stirring at 60° C. for 4 hours and the reaction trend was monitored by means of thin layer chromatography (TLC) with DCM/MeOH 9:1 as solvent (Rf=0.6). When the starting reagent had been totally consumed, the solvent was removed under vacuum giving a pale green solid which was analyzed by NMR and not purified.

Figure 17:
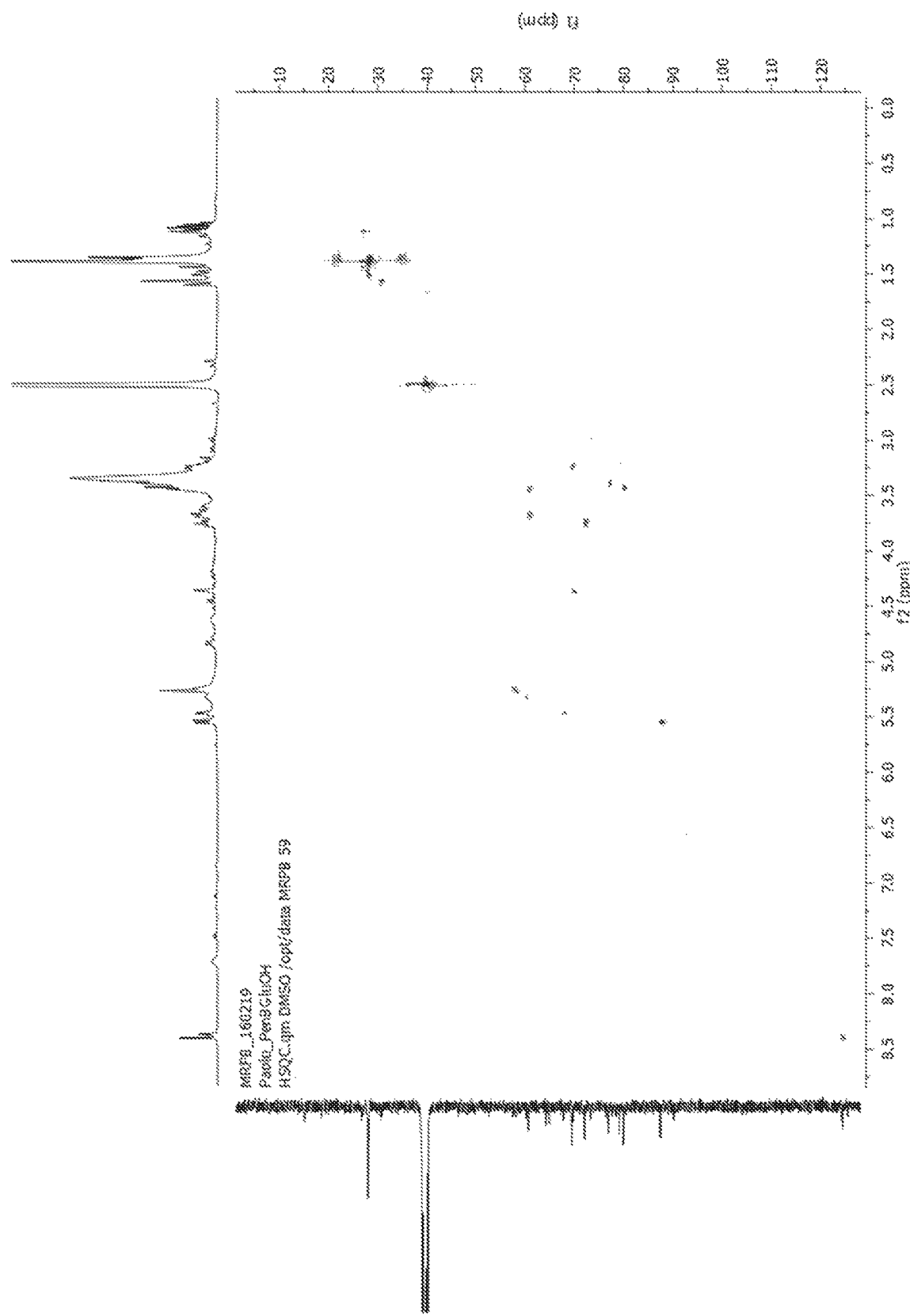
Figure 18:
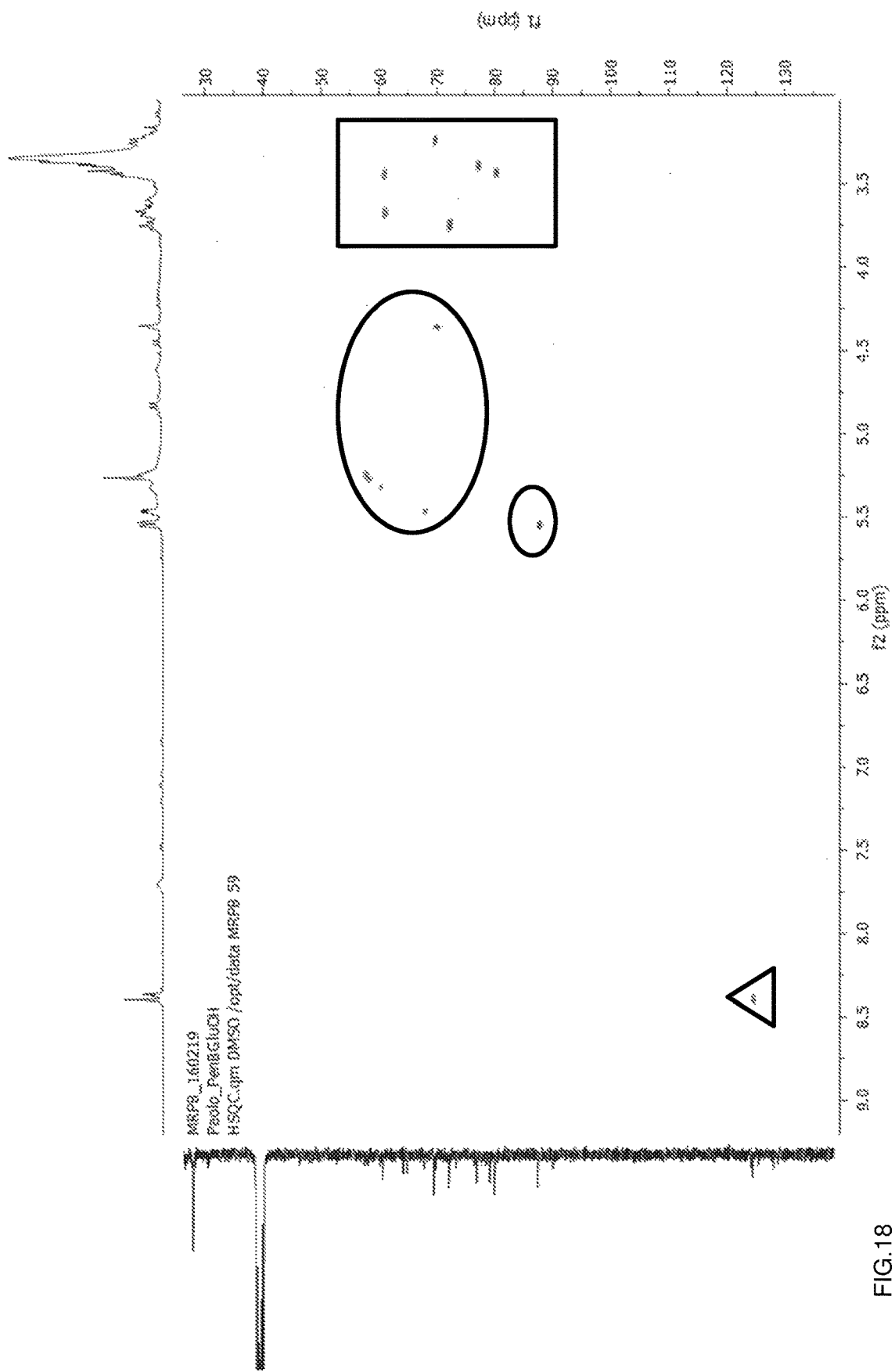
Figure 19:
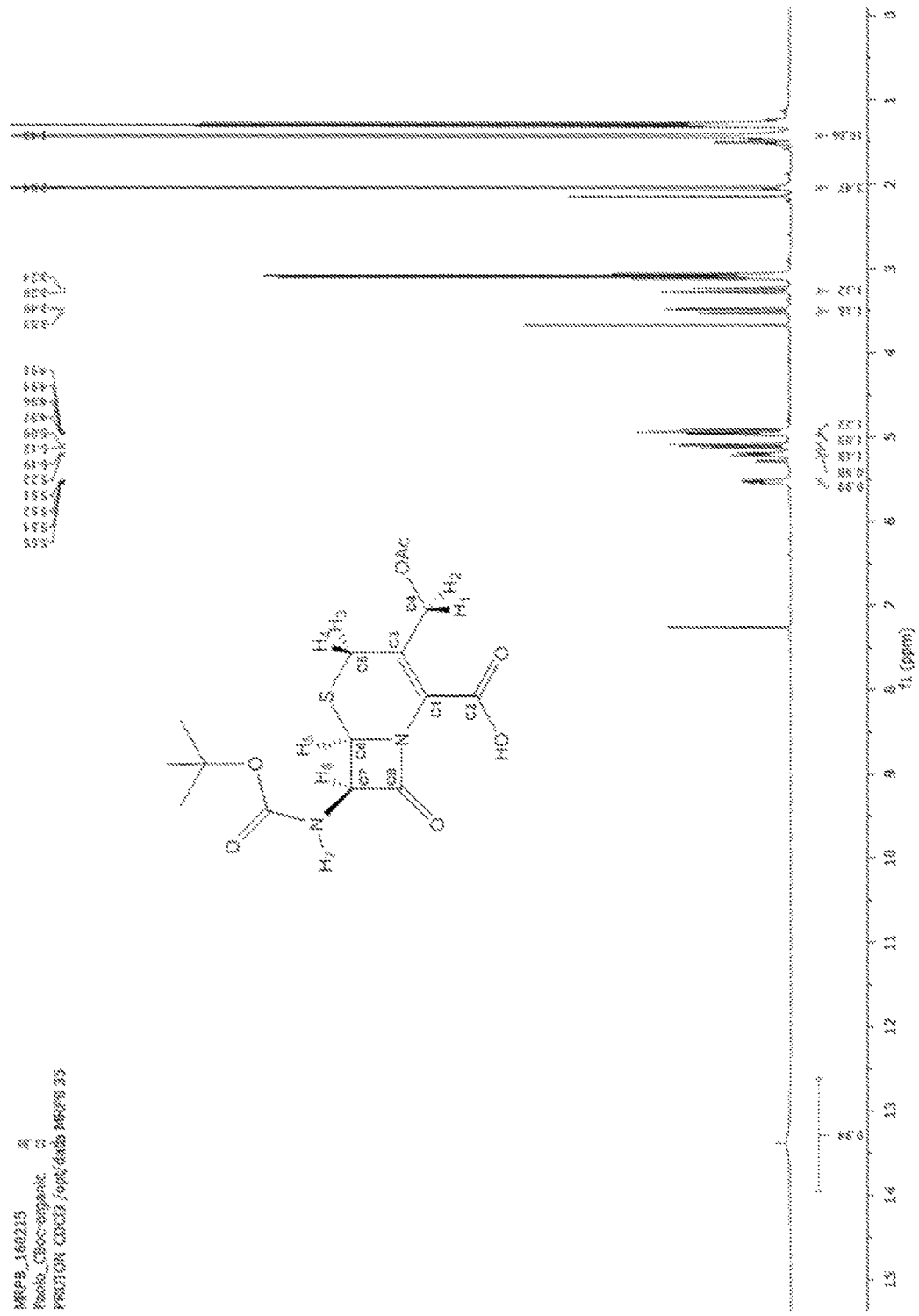
Figure 20:
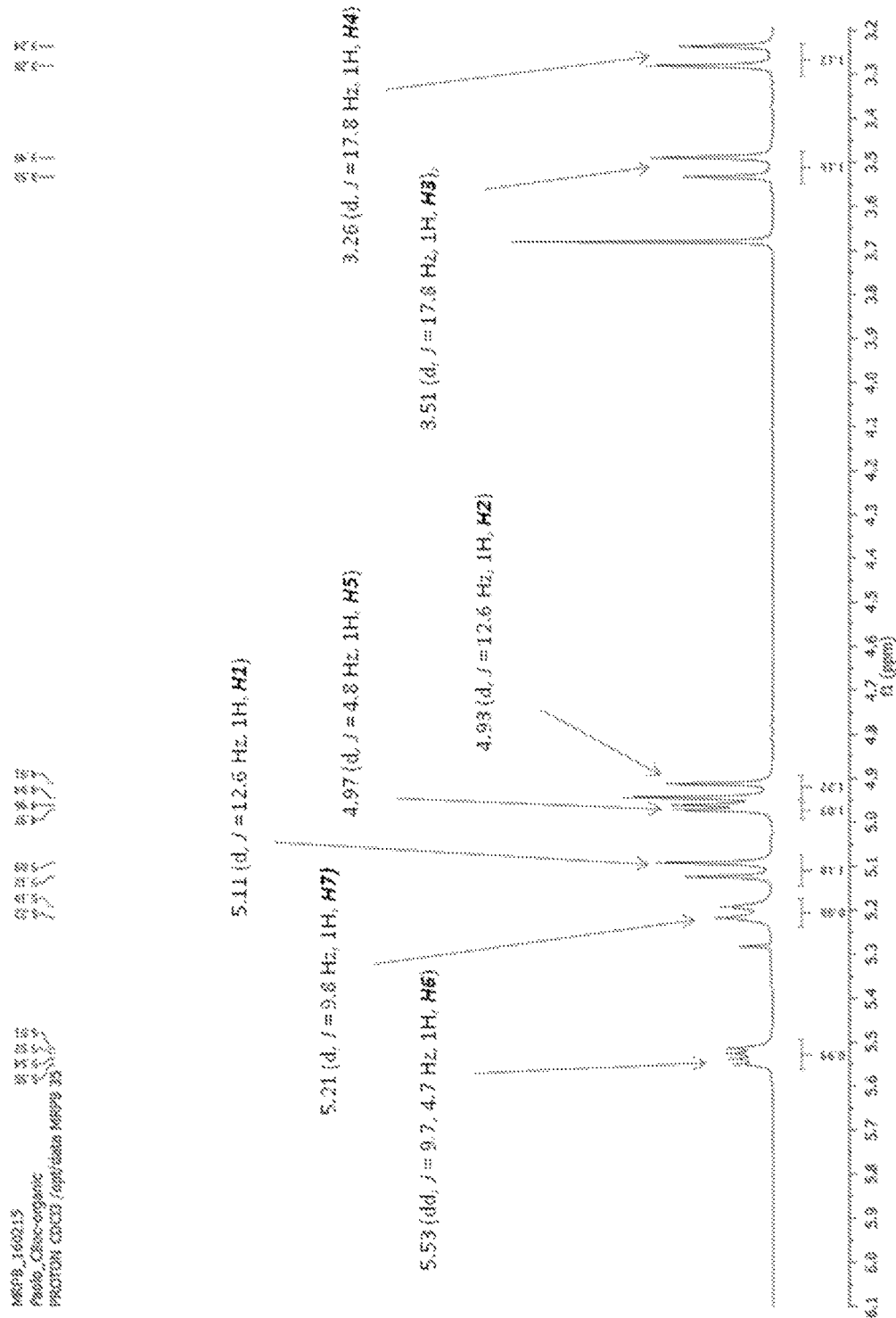
Figure 21:
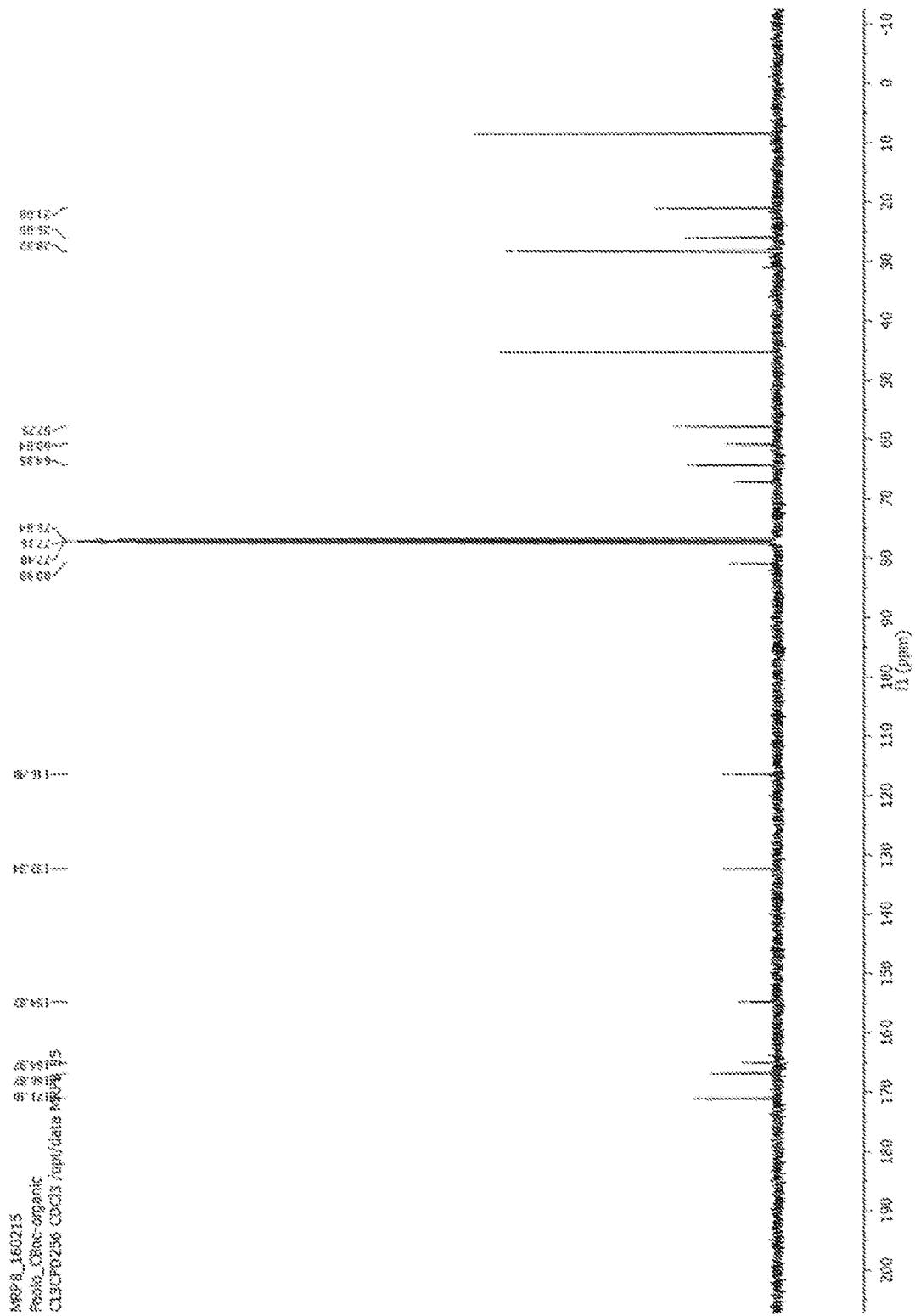
Figure 22:
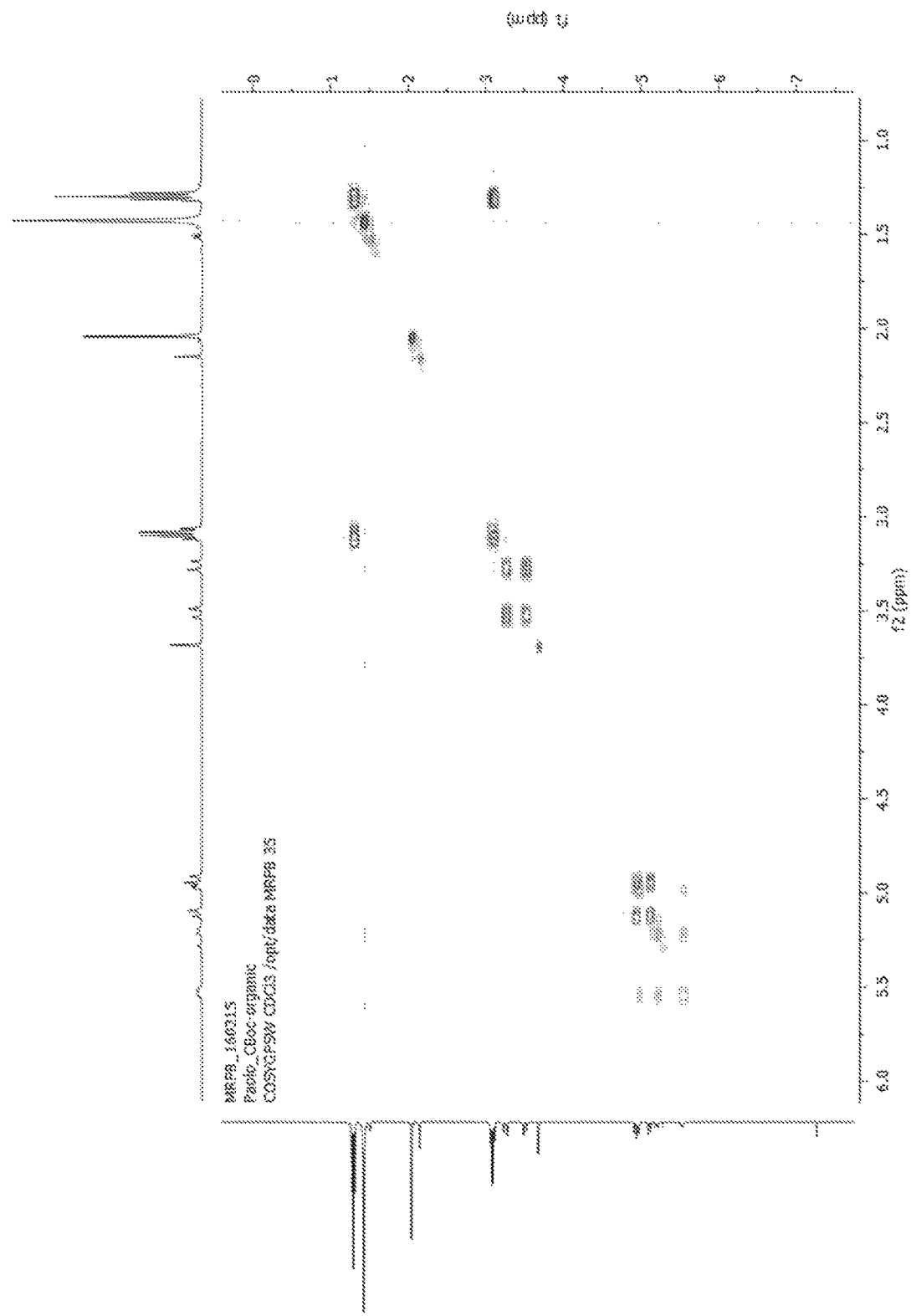
Figure 23:
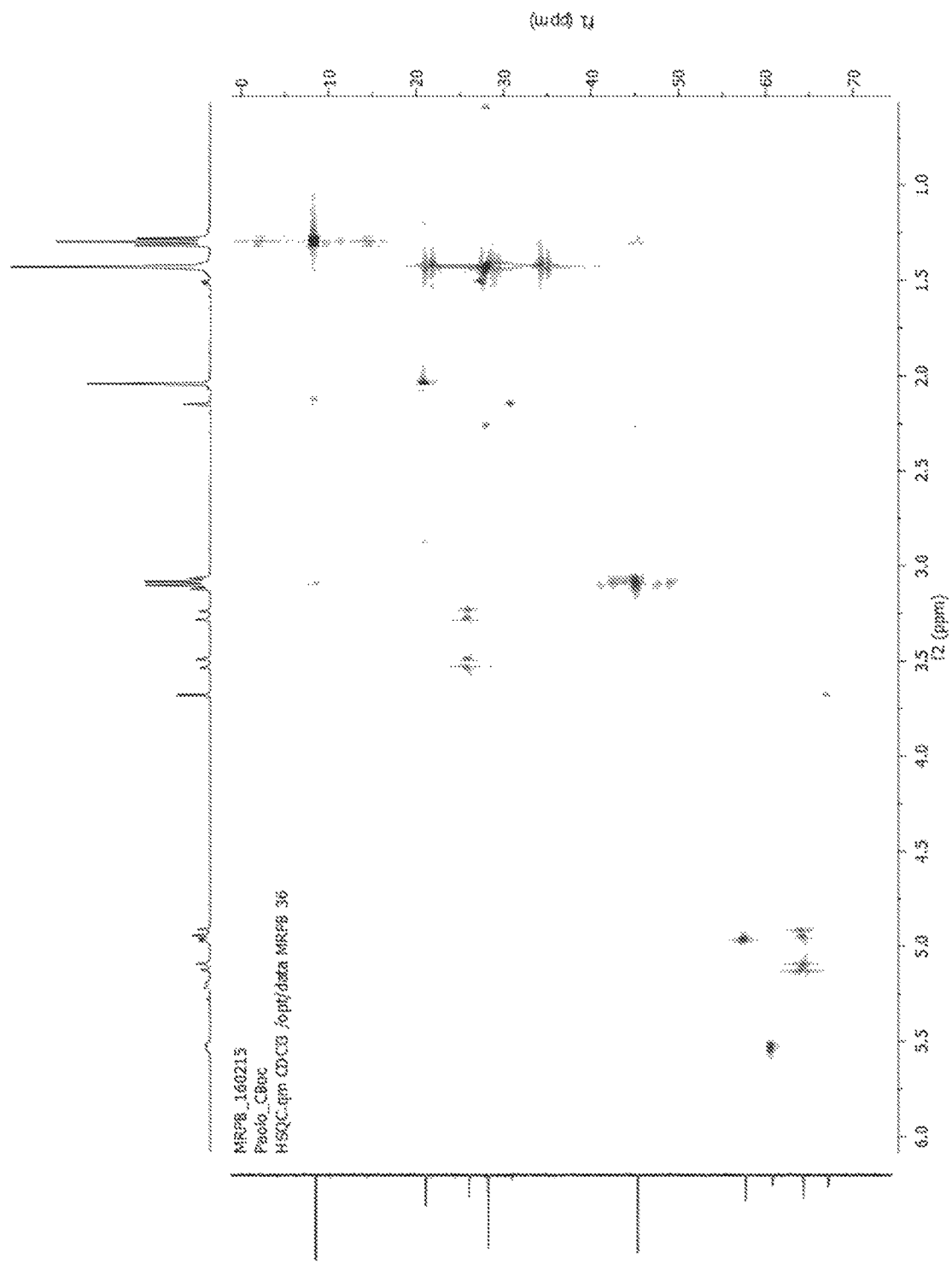
Figure 24:
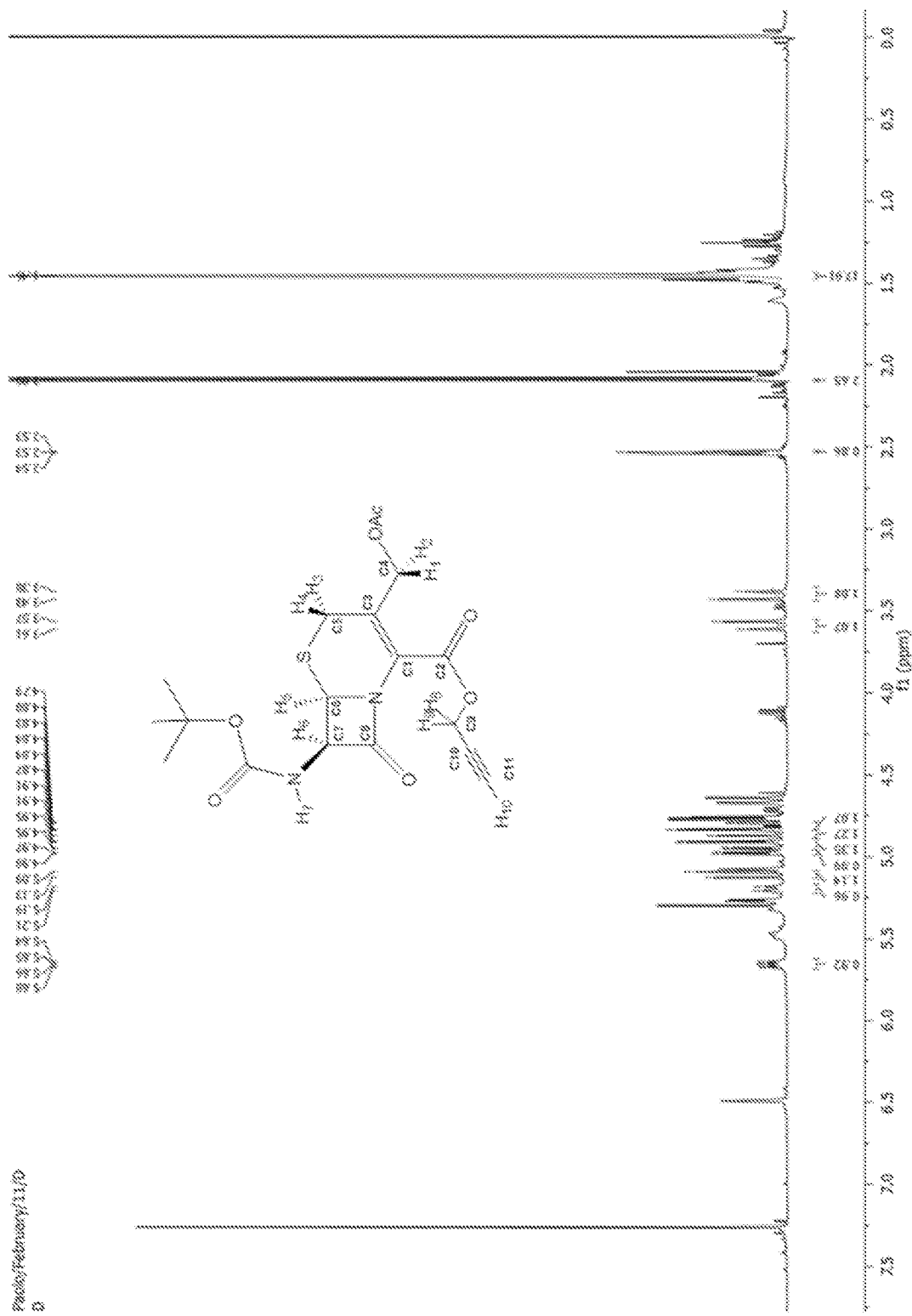
Figure 25:
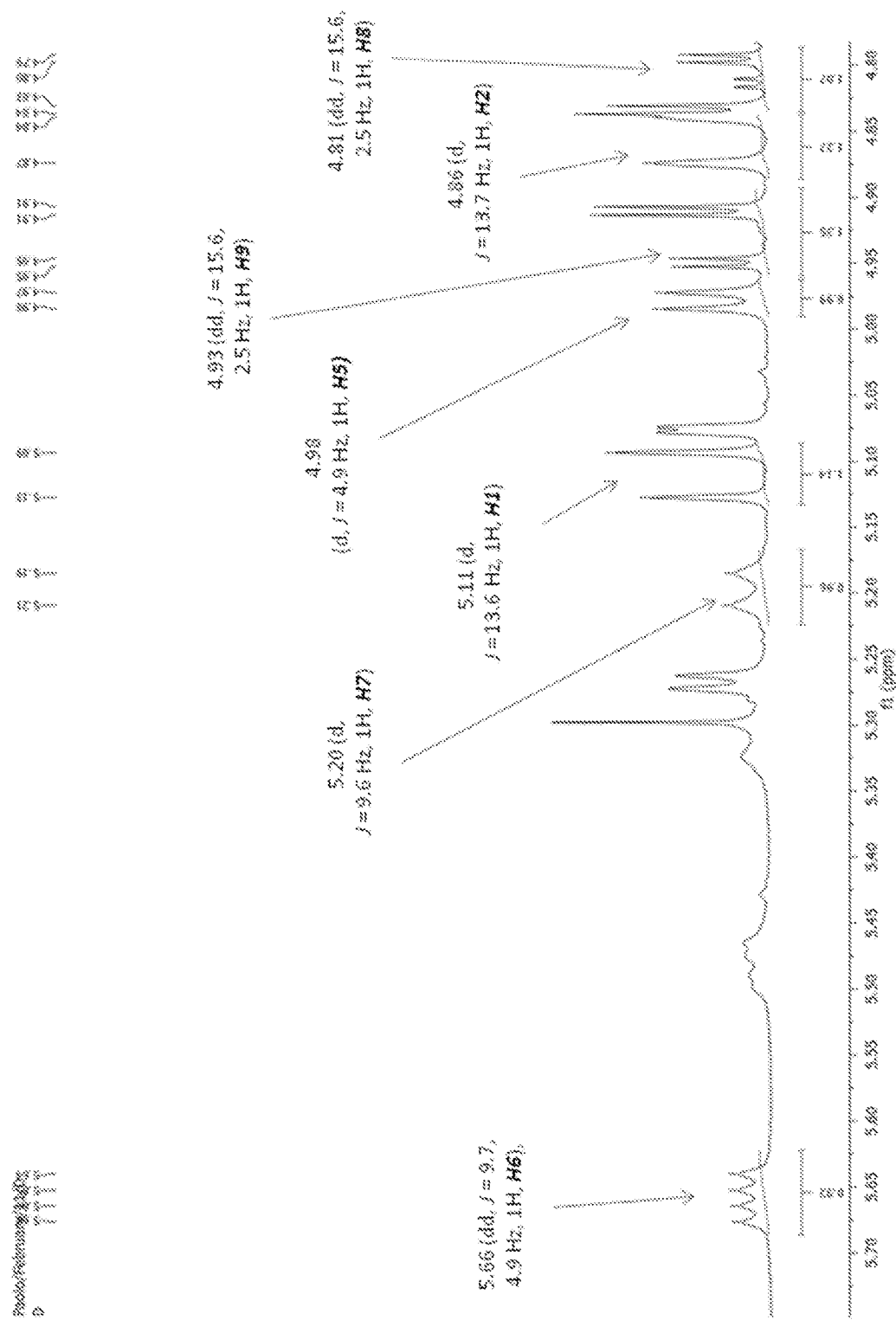
Figure 26:
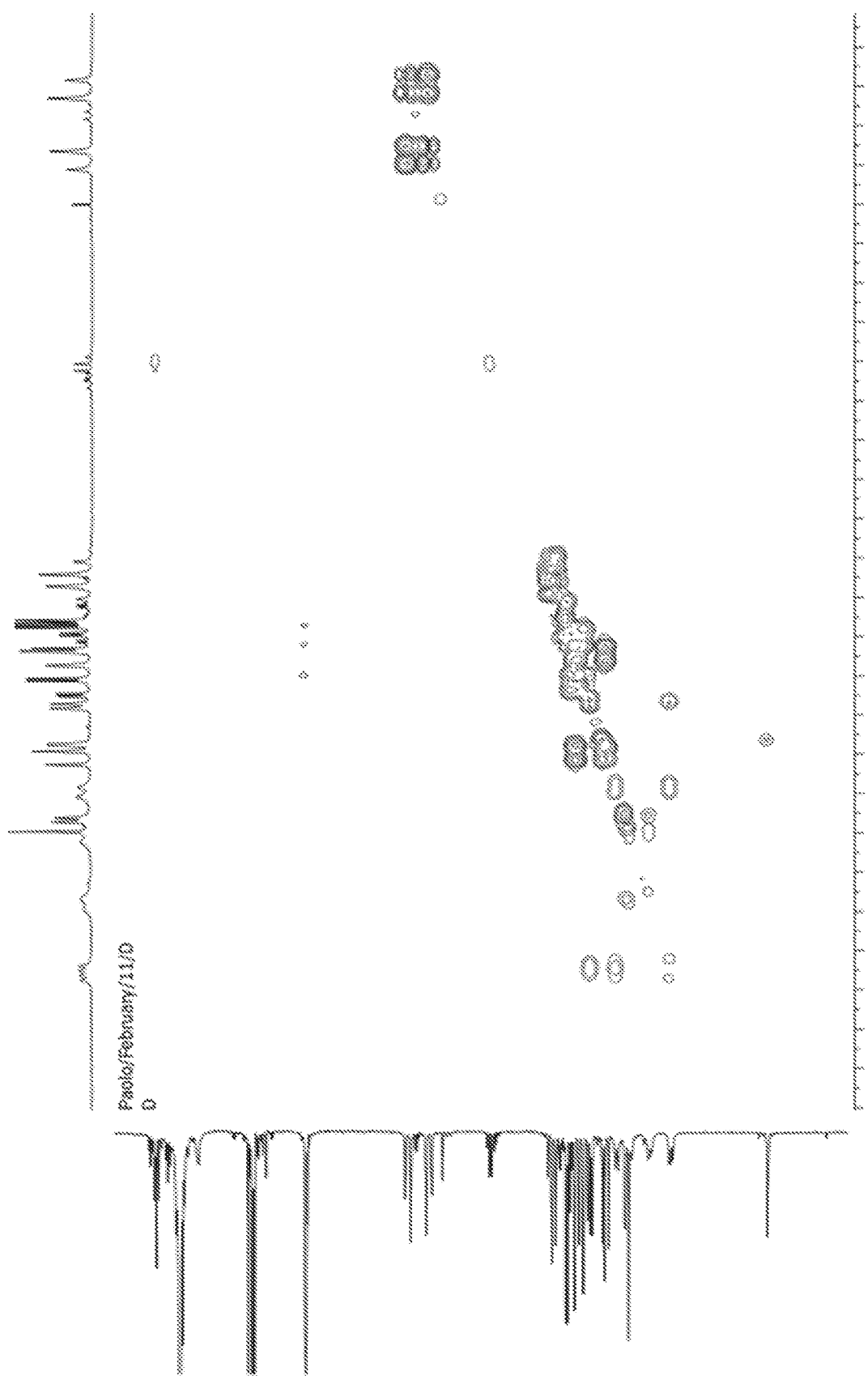
Figure 27:
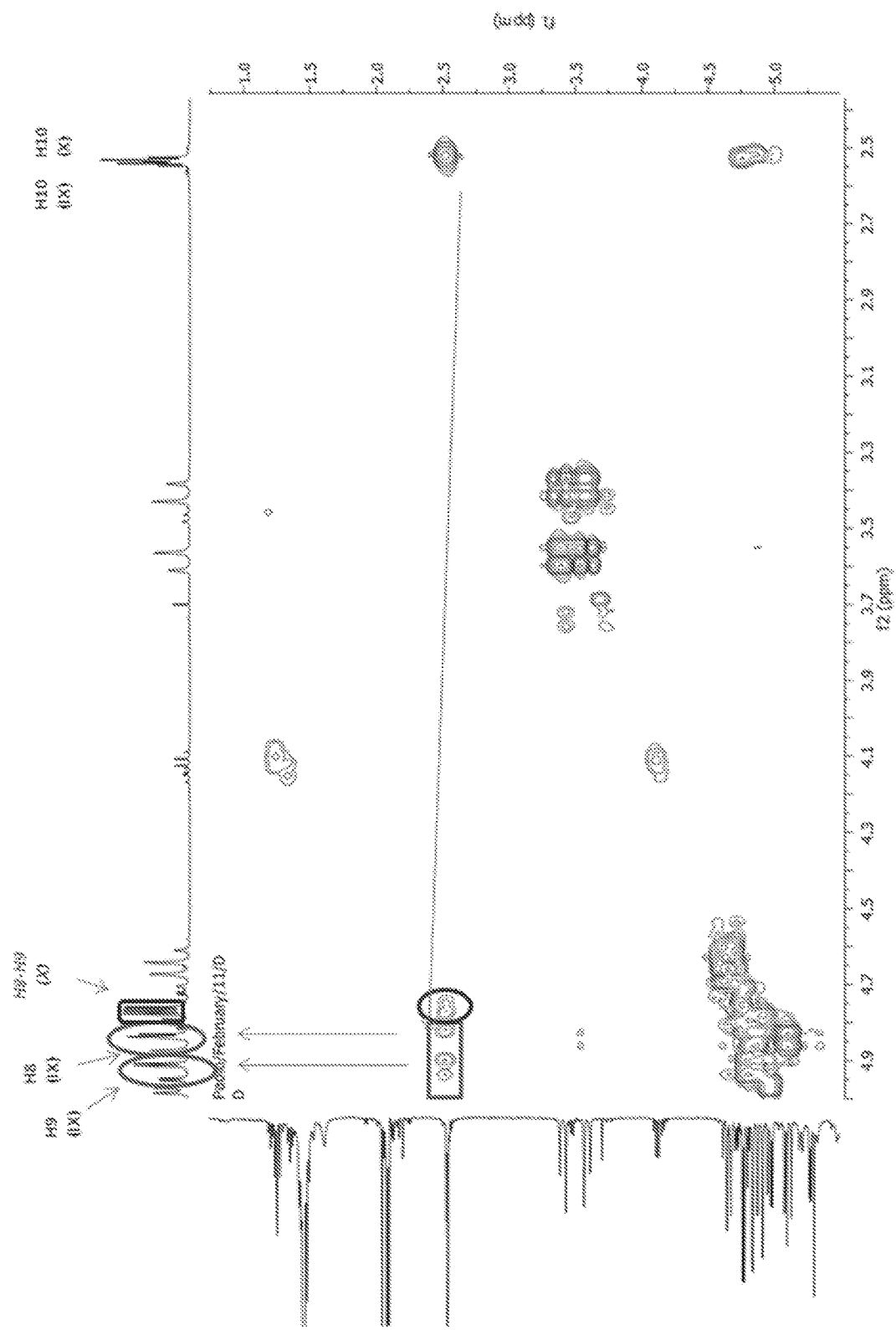

FIGS. 17 and 18 indicate the HSQC (Heteronuclear Single Quantum Correlation) spectrum in deuterated $CDCl_3$, to support the synthesis of compound (VI): in FIG. 18, in fact, the triangle indicates the carbon of the triazole, the large oval indicates the carbons of the penicillin ring and the $CH_2$ of propargyl (Blue) which has reacted with the azide. In the small oval, there is the anomeric glucose and in the rectangle, the carbons of sugar: the two blue signs indicate the carbon of $CH_2$(C-6) of glucose.

In the HSQC, the carbons having only one proton or three protons are normally red-coloured, whereas the carbons having two protons are indicated in blue.

EXAMPLE 6

Synthesis of (6R,7R)-3-(acetoxymethyl)-7-(tert-butoxy-carbonylamino)-6-oxo-5-thio-1-azabicyclo[4.2.0]oct-2-ene-2-carboxylic Acid

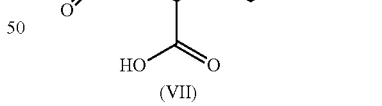

(VII)

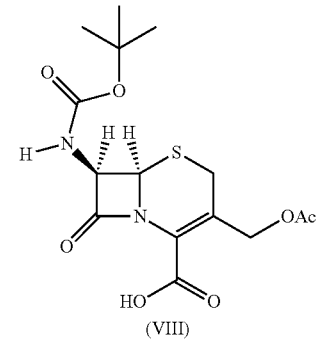

(VIII)

1 g (3.673 mmoles) of 7-ACA (7-amino-cephalosporanic acid) was suspended, in a 100 ml flask, in 30 ml of a solution of water and dioxane in a ratio of 1:1 by volume, at room temperature. After the addition of 1.023 ml (7.346 mmoles) of TEA, a complete solubilization was obtained. 1.042 g of di-tert-butyl dicarbonate (4.775 mmoles) where then added to this solution and the solution was kept under stirring at room temperature for 24 hours.

The reaction trend was monitored by means of thin layer chromatography (TLC) with DMC/methanol 9.5:0.5 as solvent and when the starting reagent had been totally consumed, the dioxane was removed by means of evaporation at reduced pressure.

The compound thus obtained was extracted using DCM (3×50 ml) and the organic phase was dried on NaSO$_4$. The organic solvent was then removed under vacuum obtaining a white foam with a yield of 90%.

The compound thus obtained was extracted using DCM (3×50 ml) and the organic phase was dried on NaSO$_4$. The aqueous phase was dried and 0.930 g of a yellow solid were obtained as a mixture of starting material and compound (VII) which was purified by means of flash chromatography obtaining a white solid with a yield of 70%.

(VIII)

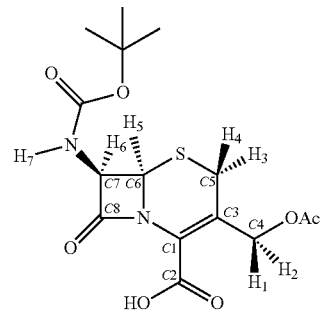

$^1$H-NMR (400 MHz, CDCl$_3$): δ 13.38 (br, 1H, COOH), 5.53 (dd, J=9.7, 4.7 Hz, 1H, H6-β-lactam), 5.21 (d, J=9.8 Hz, 1H, H7-β-lactam), 5.11 (d, J=12.6 Hz, 1H, H1-(β-lactam), 4.97 (d, J=4.8 Hz, 1H, H5-β-lactam), 4.93 (d, J=12.6 Hz, 1H, H2-β-lactam), 3.51 (d, J=17.8 Hz, 1H, H3-β-lactam), 3.26 (d, J=17.8 Hz, 1H, H4-β-lactam), 2.04 (s, 3H—CH$_3$), 1.43 (s, 9H, 3-CH$_3$).

$^{13}$C-NMR (100 MHz, CDCl3): δ 171.10 (s, 1C, CH$_3$C=O), 166.87 (s, 1C, —NC=O, C$_8$β-lactam), 164.97 (s, 1C, —OC=O, C$_2$β-lactam), 154.37 (s, 1C, C=O Boc), 132.34, (s, 1C, C$_3$β-lactam), 116.48 (s, 1C, C$_1$β-lactam), 80.98 (s, 1C, —C(CH$_3$)$_3$), 64.35 (s, 1C, C$_4$β-lactam), 60.84 (s, 1C, C$_7$β-lactam), 57.75 (s, 1C, C$_6$β-lactam), 28.32 (s, 3C, —C(CH$_3$)$_3$), 26.65 (s, 1C, C$_5$β-lactam), 21.08 (s, 1C, CH$_3$C=O)

The $^1$H-NMR $^{13}$C-NMR spectra of the compound having formula (VII) are shown in FIGS. 19-23.

EXAMPLE 7

Synthesis of (6R,7R)-prop-2-inyl 3-(acetoxymethyl)-7-(tert-butoxycarboxylamino)-8-oxo-5-thio-1-azabicyclo-[4.2.0]oct-2-ene-2-carboxylate (IX)

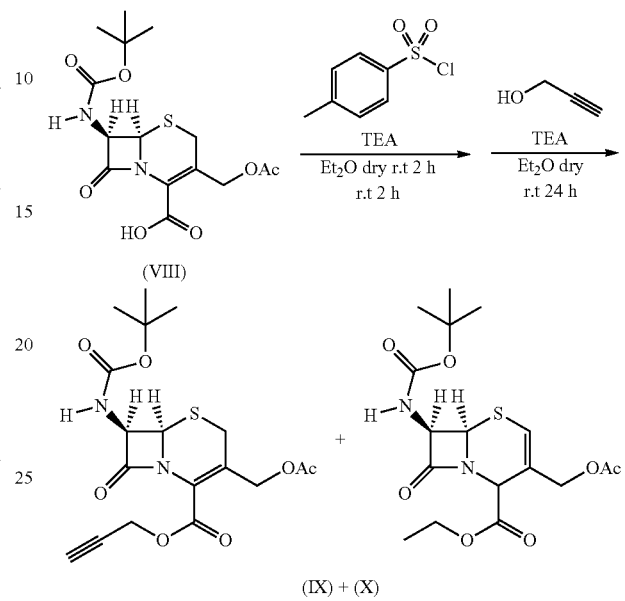

372.39 mg of (6R,7R)-3-(acetoxymethyl)-7-(tert-butoxycarboxylamino)-8-oxo-5-thio-1-azabicyclo[4.2.0]-oct-2-ene-2-carboxylic acid (1 mmole) and 139 μl (1 mmole) of anhydrous TEA (or alternatively 175 μL, of N,N diisopropylethyl amine (DIPEA)) were dissolved in 10 ml of an anhydrous mixture of Et$_2$O/DCM 7/3 (alternatively in 10 ml of anhydrous dioxane or anhydrous THF or anhydrous DCM) at 0° C. under an atmosphere of N$_2$. 190.65 mg (1 mmole) of para-toluenesulfonyl chloride (or alternatively 98 μL of methanesulfonyl chloride or 144 μL of diethylphosphate chloride) were added to the solution which was then left under stirring at room temperature for 2 hours. The formation of a white solid in the case of the mixture of ether and DCM, indicated the formation of hydrochloride of the base.

A solution composed of 57.70 ml (1 mmole) of propargyl alcohol and 139 ml (1 mmole) of anhydrous TEA (or alternatively 175 μL of DIPEA) was prepared in 3 ml of anhydrous Et$_2$O (or alternatively in DCM or anhydrous dioxane) and was added to the mixture in a single portion at room temperature. The suspension thus obtained was left under stirring in an inert atmosphere for 48 hours.

The reaction trend was monitored by means of thin layer chromatography (TLC) with DCM 9.5/Et$_2$O 0.5 as solvent (Rf=0.5) and when the starting reagent had been totally consumed, 20 ml of water were added to the reaction mixture, the compound thus obtained was extracted using diethyl ether (3×15 ml) and the organic phase was dried on Na$_2$SO$_4$. 400 mg of sticky oil, red-coloured when the activator used is para-toluenesulfonyl chloride or methanesulfonyl chloride, or greenish when the activator used is diethyl phosphate chloride, consists in the desired product (IX) (about 50%) and in the corresponding diastereoisomer X (due to the rearrangement of the double bond). The compound proved to be unstable to a purification by direct-phase flash chromatography and the pure product was still not isolated. NMR (1-H, COSY and $^{13}$C) analysis, however, confirms the presence of the desired product as indicated by the relative images. In particular, the presence of two double doublets can be observed at 4.93 ppm and 4.81 ppm with J couplings of 15.6 and 2.5 Hz relating to the two methylene protons of the propargyl introduced. At 2.5, there is the triplet typical of methane CH. The disappearance of the acid proton at 13.38 is equally important to note, indicating the formation of propargylated ester.

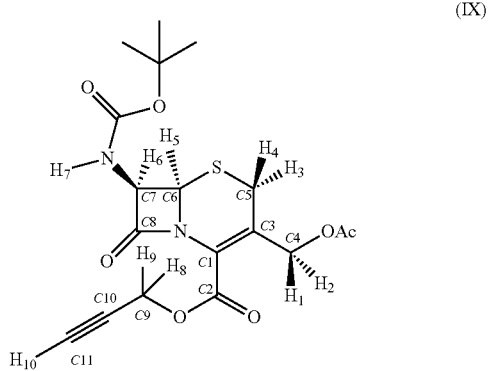

(IX)

$^1$H-NMR (400 MHz, CDCl$_3$): δ 5.66 (dd, J=9.7, 4.9 Hz, 1H, H6), 5.21 (d, J=9.8 Hz, 1H, H7), 5.11 (d, J=13.6 Hz, 1H, H1), 4.98 (d, J=4.9 Hz, 1H, H5), 4.93 (dd, J=15.6, 2.5 Hz, 1H, H9), 4.86 (d, J=13.7 Hz, 1H, H2), 4.81 (dd, J=15.6, 2.5 Hz, 1H, H8), 3.59 (d, J=18.5 Hz, 1H, H3), 3.41 (d, J=18.6 Hz, 1H, H4), 2.53 (t, J=2.5 Hz, 1H, H10), 2.09 (s, 3H, CH$_3$), 1.46 (s, 9H, 3-CH$_3$).

The non-assigned peaks belong to Compound X: more specifically, the peaks at 5.66, 5.21, 4.98 are the system H6, H7, H5; the system of CH$_2$ with respect to C9 of the propargyl group is characterized by two double doublets at 4.93 and 4.81 ppm. The value J of 15.6 Hz is coupled with the 2.5 Hz of H10 typical of alkine terminal groups. In accordance with the starting material, the system AB of CH$_2$ with respect to C5 of the ring with 6 atoms can be observed and two doublets are detected with the same coupling constant at 3.59 and 3.41 ppm. The system AB represented by the two doublets at 5.11 and 4.86 ppm can also be observed. This is the CH$_2$ of the C4. The signal at 2.5 pm is the triplet of H10, which has crossed peaks (in COSY NMR) with the CH$_2$ system represented by the two doublets at 4.93 and 4.81 ppm.

(6R,7R)-prop-2-inyl 3-(acetoxymethyl)-7-(tert-butoxy-carboxyamino)-8-oxo-5-thio-1-azabicyclo [4.2.0]oct-3-ene-2-carboxylate (X)

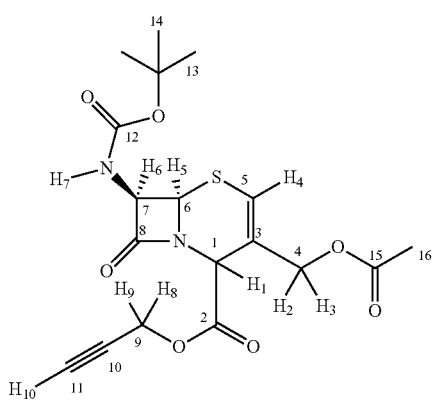

X $^1$H-NMR (400 MHz, CDCl$_3$): δ 6.48 (d, J=1.3 Hz, 1H, H4), 5.46 (dd, J=8.8, 3.2 Hz, 1H, H6), 5.34 (d, J=8.7 Hz, 1H, H7), 5.25 (d, J=3.9 Hz, 1H, H5), 5.06 (d, J=1.4 Hz, 1H, H1), 4.76 (m, 2H, H9-H8), 4.68 (d, J=12.8 Hz, 1H, H2), 4.62 (d, J=12.7 Hz, 1H, H3), 2.54 (t, J=2.4 Hz, 1H, H10) 2.07 (s, 3H, CH$_3$), 1.45 (s, 9H).

In particular, the disappearance of the proton at 13 ppm indicates that the esterification of the carboxyl group has taken place, whereas the presence of the proton at 6.48 ppm (H4) indicates that the double bond has been rearranged: this proton is a doublet with a coupling constant with H1 of 1.4-1.5 Hz. The presence of the multiplet at 4.76 ppm, which integrates 2, indicates the H9-H8 of the system of the propargyl group. In COSY, in fact, a crossed peak with the proton at 2.5 ppm (H10) is present. The two doublets with the same coupling constant J equal to 12.7 Hz are the signals of H2-H3; the impurities are therefore precisely the signals of the compound IX described above.

Figure 28:
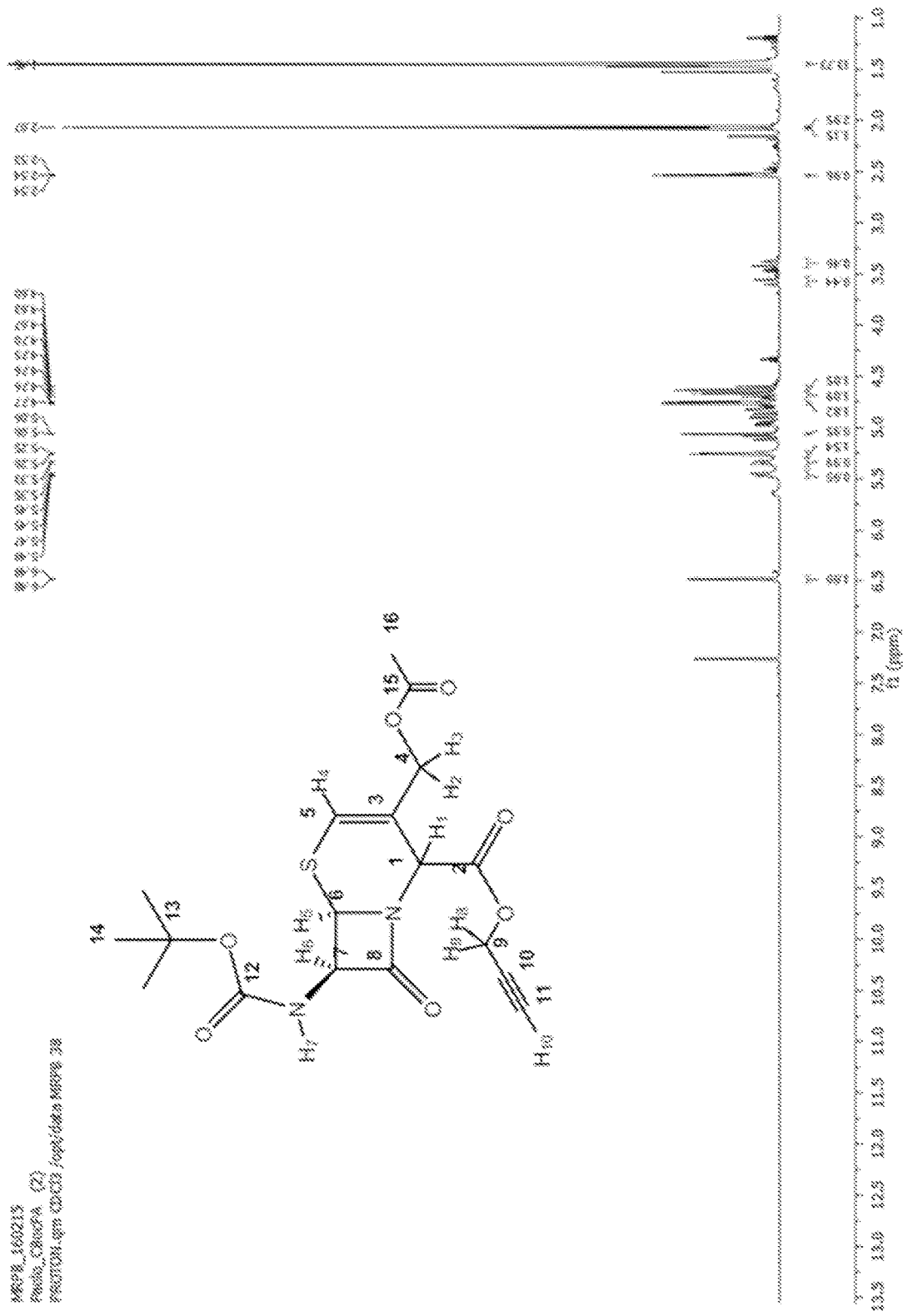
Figure 29:
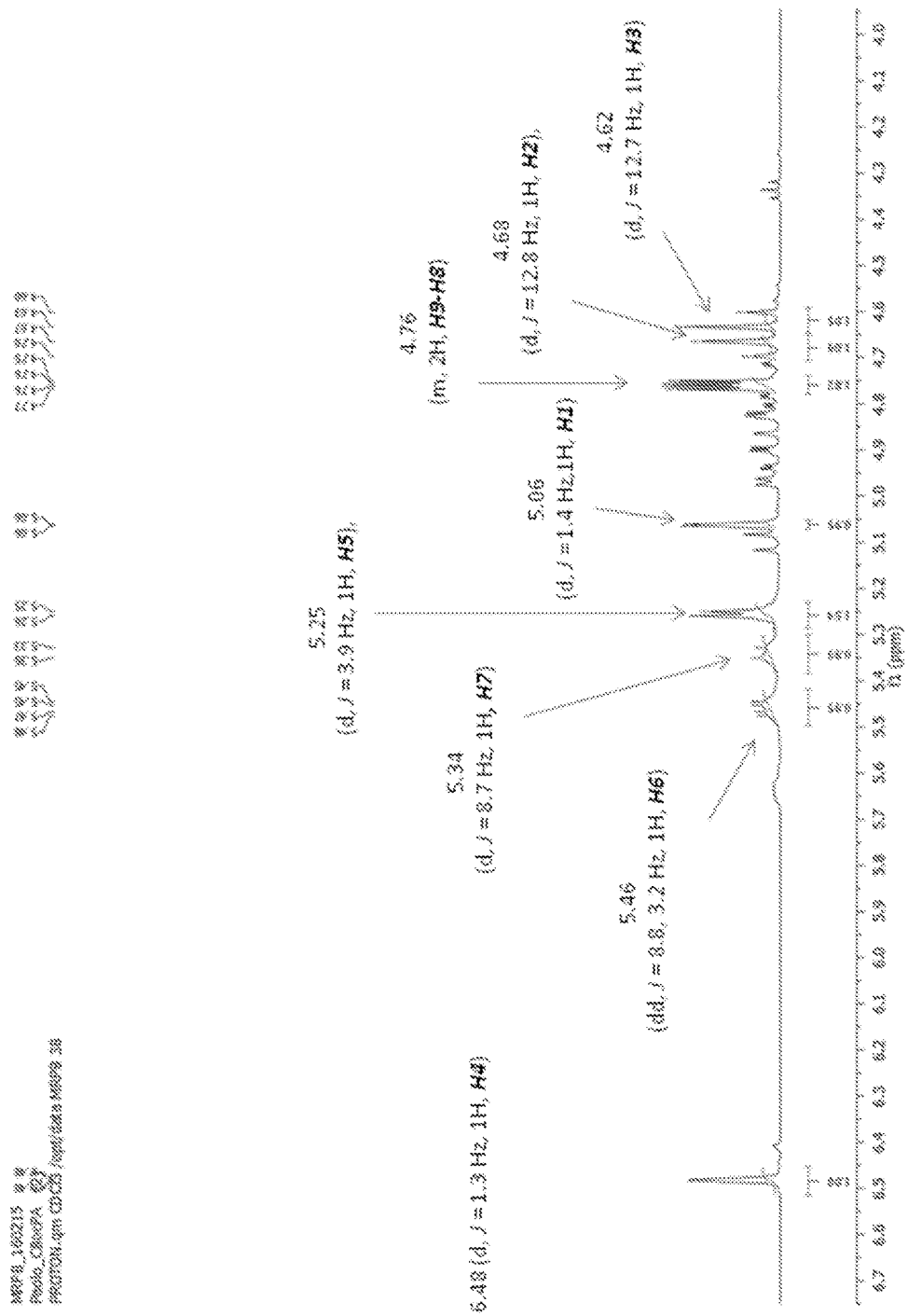

The $^1$H-NMR spectra of the compound having formula (IX) are indicated in FIGS. 24-27, whereas the $^1$H-NMR spectra of the compound having formula (X) are indicated in FIGS. 28-29.

The invention claimed is:
1. A synthesis process of triazole derivatives of β-lactam compounds, comprising the following steps:
   a) protection of the amine group of the β-lactam compound, selected from a group consisting of 6-aminopenicillanic acid and 7-aminocephalosporanic acid through the formation of a carbamate by reaction with a dicarbonate;
   b) esterification of the carboxyl group in position 2 of the β-lactam compound obtained in step a) by reaction with propargyl alcohol to obtain a precursor; and
   c) cycloaddition reaction between the precursor obtained in step b) and an organic azide, resulting in the formation of a corresponding triazole derivative of the β-lactam compound.
2. The process according to claim 1 wherein step a) is carried out by reaction with an alkyl, aromatic or cyclic dicarbonate.
3. The process according to claim 1, wherein step a) is carried out at room temperature for a time ranging from 10 to 32 hours, in a solvent which is a mixture 1:1 by volume of 1,4-dioxane and water or a mixture 1:1 by volume of tetrahydrofuran (THF) and water, and wherein the dicarbonate is di-(tert-butyl dicarbonate) being present in a molar ratio ranging from 2 to 1 with respect to the β-lactam compound.
4. The process according to claim 1 wherein step b) is carried out under anhydrous conditions using an anhydrous solvent selected from a group consisting of diethylether, 1,4-dioxane, dichloromethane (DCM), tetrahydrofuran (THF), THF in a volume ratio of 4/1 with chloroform or anhydrous DCM, in the presence of an anhydrous amine selected from a group consisting of triethylamine and dimethylaminopyridine.
5. The process according to claim 1, wherein step b) is carried out at room temperature for a time ranging from 24 to 52 hours.
6. The process according to claim 1, wherein step c) is a cycloaddition reaction mediated by copper in oxidation state I, wherein the organic azide is selected from a group consisting of tert-butyl 2-azidoethylcarbamate, 2,3,4,6-tetra-O-acetyl-β-D-glucopyranosyl azide and 2,3,4,6-OH-β-D-glucopyranosyl azide.

7. The process according to claim 1, wherein step c) is carried out in a mixture of water and C1-C3 alkyl alcohol, at a temperature ranging from 55 to 60° C., for a time ranging from 4 to 10 hours.

8. The process according to claim 1 wherein the β-lactam compound is 6-aminopenicillanic acid.

9. The process according to claim 2 wherein the alkyl, aromatic or cyclic dicarbonate is selected from di-tert-butyl dicarbonate, bis(oxyran-2-ylmethyl) dicarbonate, bis(trifluoro-methyl)dicarbonate, bis (2-ethoxycyclohexyl) dicarbonate or dibenzyl dicarbonate.

10. The process according to claim 9 wherein step a) is carried out by reaction with di-tert-butyl dicarbonate.

11. The process according to claim 3 wherein step a) is carried out at room temperature for a time equal to about 24 hours.

12. The process according to claim 3 wherein the di-(tert-butyl dicarbonate) is present in a molar ratio ranging from 1.3 to 1.

13. The process according to claim 5 wherein step b) is carried out at room temperature for a time ranging from 24 to 36 hours.

14. The process according to claim 7 wherein step c) is carried out in 1:1 by volume of water and isopropanol (IPA).

15. The process according to claim 7 wherein step c) is carried out at a temperature ranging from 58 to 60° C.

16. The process according to claim 1 wherein step c) is carried out for a time ranging from 4.5 to 6 hours.

* * * * *